US009079189B2

(12) United States Patent
Garcia et al.

(10) Patent No.: US 9,079,189 B2
(45) Date of Patent: Jul. 14, 2015

(54) METHODS AND DEVICES FOR SORTING CELLS AND OTHER BIOLOGICAL PARTICULATES

(75) Inventors: Maurice M. Garcia, San Francisco, CA (US); Aaron Ohta, Honolulu, HI (US); Ming Wu, Moraga, CA (US); Tom F. Lue, Hillsborough, CA (US); Justin Valley, Dallas, TX (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 395 days.

(21) Appl. No.: 13/250,618

(22) Filed: Sep. 30, 2011

(65) Prior Publication Data

US 2012/0118740 A1 May 17, 2012

Related U.S. Application Data

(63) Continuation of application No. PCT/US2010/029872, filed on Apr. 2, 2010.

(60) Provisional application No. 61/166,616, filed on Apr. 3, 2009, provisional application No. 61/276,999, filed on Sep. 17, 2009.

(51) Int. Cl.
*G01N 27/447* (2006.01)
*B03C 5/00* (2006.01)
*B03C 5/02* (2006.01)

(52) U.S. Cl.
CPC ............... *B03C 5/005* (2013.01); *B03C 5/026* (2013.01); *G01N 27/447* (2013.01)

(58) Field of Classification Search
CPC ....... B03C 5/005; B03C 5/026; G01N 27/447

USPC .......... 250/208.1, 559.04, 551; 204/547, 603, 204/643; 430/58.05, 60, 58.7, 70, 159, 57.5
See application file for complete search history.

(56) References Cited

U.S. PATENT DOCUMENTS 7,294,249 B2  11/2007  Gawad et al.
7,612,355 B2  11/2009  Wu et al.
(Continued)

FOREIGN PATENT DOCUMENTS

WO    2005100541 A2    10/2005

OTHER PUBLICATIONS

Dessie, S.-W., et al. "Dielectrophoretic behavior of in vitro-derived bovine metaphase II oocytes and zygotes and its relation to in vitro embryonic development competence and nRNA expression pattern" Reproduction, vol. 133, No. 3, May 2007, p. 931-946.*

(Continued)

*Primary Examiner* — J. Christopher Ball
(74) *Attorney, Agent, or Firm* — John P. O'Banion

(57) ABSTRACT

An optical pattern-driven light induced dielectrophoresis (DEP) apparatus and separation methods are described which provide for the manipulation of particles or cells and selection based on traits correlated with the DEP response. Embodiments of the apparatus use DEP electric field patterns in combination with microfluidic laminar flows to measure response, separate, segregate and extract particles from heterogeneous mixtures according to the relative response of the particles to one or more DEP fields without damaging living cells. The methods are particularly suited for selecting and extracting the best sperm and embryo candidates based on fitness for use with existing artificial reproduction procedures and excluding defective or non-viable gametes.

55 Claims, 11 Drawing Sheets

(56) References Cited

U.S. PATENT DOCUMENTS

2003/0224528 A1 12/2003 Chiou et al.
2005/0173313 A1 8/2005 Tyvoll et al.
2007/0095669 A1 5/2007 Lau et al.
2009/0170186 A1 7/2009 Wu et al.

OTHER PUBLICATIONS

International Search Report and Written Opinion from related PCT Application No. PCT/US2010/029872, issued on Jan. 31, 2011 (pp. 1-8), with claims searched (pp. 9-23), pp. 1-23.

* cited by examiner

METHODS AND DEVICES FOR SORTING CELLS AND OTHER BIOLOGICAL PARTICULATES

CROSS-REFERENCE TO RELATED APPLICATIONS

This application a 35 U.S.C. §111(a) continuation of PCT international application number PCT/US2010/029872 filed on Apr. 2, 2010, incorporated herein by reference in its entirety, which is a nonprovisional of U.S. provisional patent application Ser. No. 61/166,616 filed on Apr. 3, 2009, incorporated herein by reference in its entirety, and a nonprovisional of U.S. provisional patent application Ser. No. 61/276,999 filed on Sep. 17, 2009, incorporated herein by reference in its entirety. Priority is claimed to each of the foregoing applications.

The above-referenced PCT international application was published as PCT International Publication No. WO 2010/115167 on Oct. 7, 2010 and republished on Mar. 31, 2011, and is incorporated herein by reference in its entirety.

This application is related to U.S. Pat. No. 7,612,355 issued on Nov. 3, 2009, incorporated herein by reference in its entirety. This application is also related to United States Patent Application Publication No. US 2009/0170186 A1, published on Jul. 2, 2009, incorporated herein by reference in its entirety. This application is also related to PCT International Publication No. WO 2005/100541 A2 published on Oct. 27, 2005, incorporated herein by reference in its entirety.

STATEMENT REGARDING FEDERALLY SPONSORED RESEARCH OR DEVELOPMENT

This invention was made with government support under Grant Numbers RR024131, EY018228, HD053943, and HD069462 awarded by the National Institutes of Health (NIH). The government has certain rights in the invention.

INCORPORATION-BY-REFERENCE OF MATERIAL SUBMITTED ON A COMPACT DISC

Not Applicable

BACKGROUND OF THE INVENTION

1. Field of the Invention

This invention pertains generally to devices and methods for sifting components of heterogeneous mixtures, and more particularly to devices and methods for separating and quantifying biological particulates with different physiological states with an optoelectronic tweezers and dielectrophoresis (OET-DEP) separation scheme.

2. Description of Related Art

The efficient separation of biological particulates such as stem cells, embryos or bacteria from isolates without damaging the particulates is an important step in a variety of diagnostic and treatment methods.

There are a variety of applications where it is desirable to sort heterogeneous populations of cells. One example is the sorting of adult stem cell populations based on cell viability. It may be desirable to exclude dead or minimally viable stem cells from living, more hearty/viable cells, for use in human and/or animal stem cell medical therapeutics, reproductive-assistance interventions, genetic-screening of gametes, and in preparation for cell "banking" (cell storage by cryogenic or other modalities).

Another example is the sorting of non-motile viable sperm from non-motile non-viable sperm. In a subset of infertile human patients or animals, where nearly all sperm are non-motile, it is desirable to sort viable from dead sperm, for use with "in-vitro" insemination procedures. The limitation encountered with present technologies and modalities is that it is not possible to use the same sperm that have been sorted into "non-motile/live" and "non-motile/dead" groups, because either the sorting modality is lethal to the sperm, or, because it poses unacceptable risk of genetic damage to the sorted sperm so as to preclude using the same sperm, if found to be "viable", for fertilization.

A further useful sorting would be the sorting of cells based on chromosome number, such as for screening to exclude gametes with an abnormal number of chromosomes or sorting of cells based on chromosome structural damage. Specific examples include normal chromosome damage due to cell aging or acquired cell damage from various cell processing techniques, radiation, chemotherapy, and iatrogenic tissue injury.

Sorting of cells based on genetic mutations, despite otherwise "intact" chromosome structure is also desirable. Examples include genetic mutations that code for aberrant proteins and/or protein structures that give rise to syndromes/disease states of a living organism. One illustration is the Cystic Fibrosis (CF) mutation, which causes CF, a common hereditary disease caused by mutations of the gene encoding cystic fibrosis transmembrane conductance regulator (CFTR), a cAMP-activated anion channel, with clinical manifestations of progressive lung disease, pancreatic insufficiency, and infertility in both sexes. CF is one of the most significant life-shortening autosomal recessive disorders found in Caucasians worldwide.

Sorting of cells based on the type of chromosome(s) contained within the cell may also be useful. For example, gamete "sex-sorting" for use in assisted-reproduction techniques, where the pre-selection the sex of the offspring is desirable or where it is essential that the sex of the offspring is ensured to be either male or female, in order to avoid propagation of sex-specific genetic disorders/diseases.

Accordingly, the separation of live cells from dead cells, cancer cells from normal cells or gram-positive from gram-negative bacteria can be important for diagnostic and therapeutic treatments. These applications require that cells not only be sorted efficiently and into a fine spectrum of groups, but also that the cells can be retrieved for use at the end of the sorting procedure.

Existing approaches to cell sorting are often labor intensive and create damage risks to the cells being sorted from mechanical forces, or chemical exposures. For example, physical or genetic damage may occur through mechanical sorting (i.e. the use of filter systems) or flow Cytometry assays or differential uptake of chemicals ("cell viability" assays).

In contrast to other techniques used to sort particles, dielectrophoresis (DEP) does not require that the cell be motile; the presence or knowledge of cell surface antigens; or the use of external materials, such as antibodies or chemicals to aid visualization. Dielectrophoresis refers to the motion of neutral particles as a result of the application of an external non-uniform electric field. Unlike linear electrophoresis, DEP does not require the object to have a net charge.

A non-uniform electric field interacts with an induced dipole in the particle and the particle can experience a dielectrophoretic force toward a region of high field intensity (positive dielectrophoresis) or toward a region of low field intensity (negative dielectrophoresis). In other words, the DEP forces attract some particles and repel other particles. The phenomenon can be observed with either AC or DC electric fields because dielectrophoretic forces do not depend on the polarity of the electric field. Therefore, the motion of the particle is not a result of its polarity but of the magnitude of the electric field.

Previous devices use a DEP field that has been generated by a "fixed electrode" embedded within a micro-chamber filled with a minimally conductive solution and particles to be studied. Each electrode is independent and connected to a source of alternating current, and thus generates a DEP field at its location. This "fixed electrode" design does allow one to use DEP to "trap" a particle so that it can be visually examined, or, to examine which cells travel toward the electrode. However, the "fixed electrode" design is extremely limited. Fixed electrodes also require costly microfabrication, produce bubbles and electrolysis products that can harm device operation, and can damage cells with their strong field gradients.

For example, to "study" even a small group of cells, each cell must be manually isolated and delivered to the fixed DEP field. This reliance on delivering each cell to the source of the DEP field is very labor intensive, and creates the risk that the cells being studied will be damaged during such extensive manipulation.

Another limitation of the "fixed electrode" design is that because the source of DEP is fixed in space, it cannot be moved. Therefore, it is very difficult to measure the attraction each particle for the DEP field. The cell must be placed a distance away from the DEP electrode, to see how fast it moves towards the electrode. Such measurements are compromised by the fact that the DEP field diminishes with distance. Therefore, the DEP field that a particle experiences a given distance away from the electrode is, by definition, different from what experiences closer or further away. The effect of distance from the electrode, on the DEP field strength the particle experiences can be accounted for by mathematical models, but this is tedious, and introduces the possibility of systematic and random measurement errors.

Living cells can be described as "dielectric" objects because they can be electrically polarized in an electric field due to their inherent electric gradients. Living cells maintain electrical gradients across their semi-permeable cell membranes. The dielectric potential of any cell has been shown to depend on its physiologic status; composition (e.g., charged membrane structures, cytoplasm contents, organelles, and charged protein and DNA); morphology; and phenotype, in addition to the frequency of the applied electrical field. Therefore, the same cell type in different physiological states (which differ with respect to the latter factors define the dielectric potential) will possess distinctly different dielectric potentials, which in turn can be utilized for separation.

Accordingly, there is a need for Micro-fluidic cell-sorting chip designs to facilitate sorting of heterogeneous populations of living and dead cells as well as select by viability, cell size, magnitude of cell membrane dipole, and features of the cell's chromosome content, such as chromosome number, degree of chromosome damage, chromosome type (gamete sex-sorting), and genetic aberrations of known and unknown diseases. There is also a need for sorting devices that are high through-put and sort cells into a spectrum rather than just two groups. There is a further need for devices that can retrieve the sorted cells.

The present invention satisfies the need for greater sorting throughput, greater sorting specificity, and the efficient retrieval of the sorted product and is generally an improvement over the art.

BRIEF SUMMARY OF THE INVENTION

The present invention is directed to performing particle and cell separations and extractions from a heterogeneous mixtures using optical pattern-driven light induced dielectrophoresis (DEP) and methods for correlating particle characteristics with the relative response to DEP fields. Because the OET-DEP fields are generated from an optical pattern, which can be projected anywhere, it is possible to use OET DEP as "virtual" microelectrodes that can be manipulated by location, time dimension and field intensity with light frequency and intensity and are preferred. Since the area of the projected optical pattern can be varied as desired, smaller patterns can be used to assay and sort individual cells. Alternatively, the larger optical patterns can be swept over a microscope field-of-view for parallel higher-throughput sorting.

In accordance with one embodiment of the invention, an optical pattern-driven dielectrophoresis apparatus and method is described for patterning electric fields on a photoconductive surface for separating and extracting single particles or collections of particles in conjunction with a flow of liquid is provided. The ultimate virtual electrode resolution is determined by the optical diffraction limit. In addition, the induced OET-DEP force is proportional to the gradient of the square of the electric field, making it well confined to the local area of the virtual electrodes, which is also important for single particle manipulation. A wide variety of light sources can be utilized, such as coherent and incoherent light, and single or multistage manipulation of particles can be readily achieved.

In one embodiment, a structure according to the present invention has two surfaces: a top electrode surface and a bottom photoconductive surface with side walls forming a chamber with input and output ducts. Liquid media containing the particles of interest is disposed between the two surfaces. An AC voltage is applied across the two surfaces and, when light shines on the photoconductive surface, a virtual electrode is induced and the ionic charges at the double layer at the solid-liquid interface couple with the applied electric field trapping the particles in the illuminated spots. The illuminated spots move across the chamber to an output flow of buffer and the particles are released to the output flow for extraction.

In another embodiment, parallel flows of fluid flow across one or more DEP electrodes that attract particles of interest. The virtual electrodes can be arranged in sequence with progressively larger field intensities. The optical patterns can move from one flow to the other so that attracted cells are delivered to the output flow and the unaffected particles continue to a waste output. Particles responding to the electrodes with the stronger DEP intensity fields can be sequentially recovered or by their position in the output effluent over time if the whole pattern is moved at one time. Non-responsive particles of interest can also be separated from responsive particles that are moved to the second flow in this embodiment.

Another embodiment provides a fluid flow containing particles that slows in a gradually expanding separation chamber with one or more elongate light patterned electrodes preferably at an angle to the fluid flow. The light pattern can be a series of rectangular shapes and the intensities of the resulting fields can increase or decrease along the sequence so that a particle in the fluid flow experiences increasing or decreasing DEP fields.

A further embodiment provides an input fluidic channel opening to a separation chamber with at least one DEP electrode shaped to have increasing intensity. Upon being trapped within the light-pattern, cells experiencing increasing attractive force will migrate downward along the light pattern until the OET-induced force is less than the net force from the microfluidic flow. At this point, the cells will no longer be trapped by the light pattern, and will flow into the corresponding output channel.

The methods of the present invention are particularly suited for selecting and extracting the best sperm and embryo candidates based on fitness for use with existing artificial reproduction procedures and excluding defective or non-viable gametes or identifying the best stem cells for use in a variety of procedures. All of the sorting platform configurations discussed above can be used to sort any single cell (e.g. sperm, oocytes, or somatic cells, human or animal) or multicellular structures (e.g. a relatively early stage embryo, human or animal).

It was observed with human sperm samples that there was a significant range in the magnitude of positive response that "live" cells exhibited towards DEP. This suggested that DEP was capable of sorting sperm not only on the basis of their absolute response (absolute viability—live or dead), but also on the basis of their relative response to DEP (index of relative viability-health or viability). The observed spectrum of responses to OET-DEP among confirmed viable, non-motile sperm, suggests sample heterogeneity with respect to "quality" (defined as relative viability). Since the OET-DEP response predicts "viability" then the observed relative differences in OET response predict relative differences in viability, which, is essentially defined as "health."

Furthermore, selection of optimal quality embryos for in vitro fertilization (IVF) transfer is critical to successful live birth outcomes. At the present time, embryos are chosen based on a subjective assessment of morphologic developmental maturity. Pre-implantation embryo cleavage rates in vitro are an index of embryo health or viability. It has been shown that an embryo's DEP response is highly correlated with its developmental stage. It is therefore possible to select and extract the most developmentally mature embryos among a mixed cohort of morphologically indistinguishable embryos.

As embryos age (1-cell to 2-cell to 4-cell . . . ) the DEP response of the embryo progresses from positive (attractive) to negative (repulsive). This dichotomy in response allows the user to accurately, and systematically assess the morphological state of the embryo. Therefore, among a cohort of embryos this technique can select out the most developmentally mature embryo for implantation (it is assumed that the faster developing embryos are likely to be the most viable upon implantation).

Accordingly, it is possible to select the healthiest and most suitable gamete cells for artificial fertilization procedures as well as the most suitable embryos for implantation that selects from a population of morphologically similar particles. The methods are non-invasive and selectively exclude defective, damaged or less fit gametes or embryos and permit the use of the most suitable gametes and embryos and create optimum conditions for successful implantation.

An aspect of the invention is to provide an apparatus and methods that are non-invasive that can accurately discriminate viable cells from non-viable cells and/or identify the healthiest cells among a population of viable cells can be identified, for selection and physical extraction.

Another aspect of the invention is an OET-DEP device that sorting chamber that integrates with microfluidic devices, such as channels, cavities, reservoirs, and pumps.

A still further aspect of the invention is to provide a method for sorting the gametes and embryos that are most suitable to improve the success rate of artificial fertilization techniques.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes several embodiments of the present invention are depicted in the apparatus generally shown in FIG. 1 through FIG. 8 and the associated methods. It will be appreciated that the methods may vary as to the specific steps and sequence and the apparatus may vary as to structural details, without departing from the basic concepts as disclosed herein. The method steps are merely exemplary of the order these steps may occur. The steps may occur in any order that is desired, such that it still performs the goals of the claimed invention.

The present invention provides and apparatus and method for separating and extracting specific cells with selected traits from a heterogeneous mixture of cells or particles. Such traits may include viability, fitness for a particular purpose, chromosome composition or an identified defect.

Figure 1:
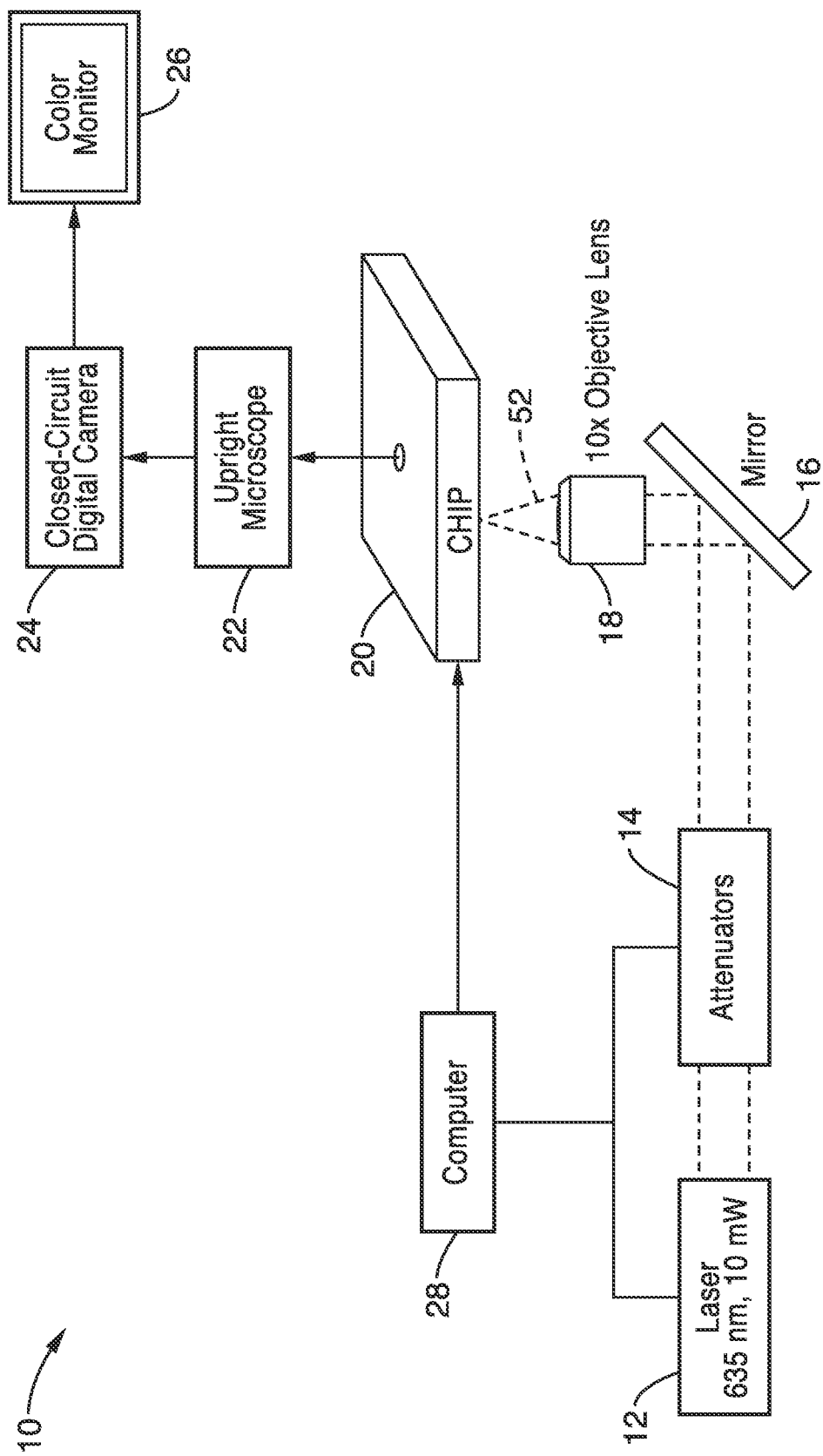
FIG. 1 is a schematic drawing of one embodiment of an OET-DEP cell sorting platform according to the invention.
Figure 2:
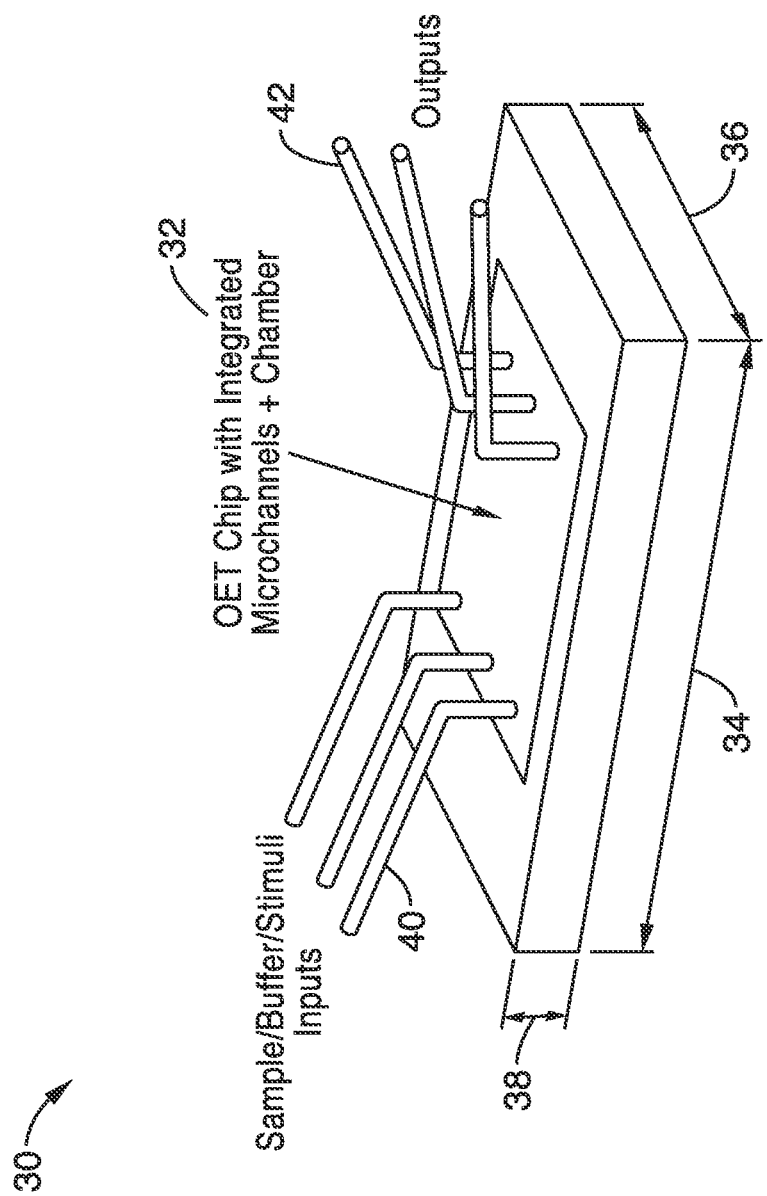
FIG. 2 is a perspective schematic view of one embodiment of an OET-DEP chip that may be used with the cell sorting platform shown in FIG. 1.
Figure 3:
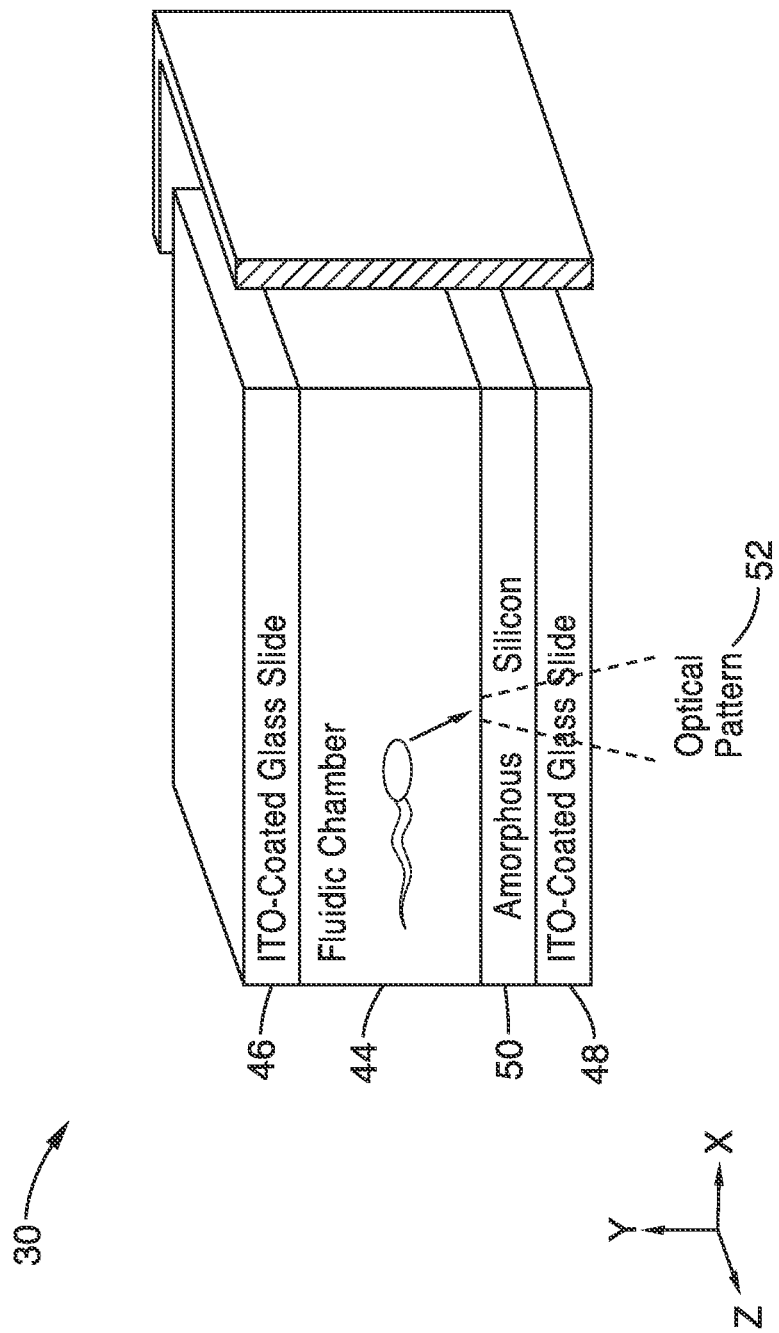
FIG. 3 is a schematic cross sectional view of one embodiment of an OET-DEP chip according to the invention.

Referring first to FIG. 1 through FIG. 3, a schematic of one embodiment of an OET-DEP cell sorting platform apparatus according to the invention is generally shown. In FIG. 2, a perspective schematic view of one embodiment of an OET-DEP chip that may be used with the cell sorting platform shown in FIG. 1 as a general illustration of an OET-DEP separation chip. FIG. 3 is a schematic cross sectional view of one embodiment of an OET-DEP chip according to the invention to shown the general structure of a separation chamber.

FIG. 1 illustrates an example embodiment 10 of a system configuration for optical sorting of microscopic particles. In this example, a laser light source 12 is used with attenuators 14 to provide a light pattern. The pattern is directed though a mirror and through a 10× objective lens 18 to designated points on chip 20.

Although a laser light source configuration is provided as an illustration, it will be understood that the source of light patterns can be from a variety of sources. For example, a single-mode fiber pigtailed laser diode with a wavelength of 635 nm coupled through a fiber collimator producing a beam spot size of 3 mm and an optical power of 120 µW could be used.

In another embodiment, the light is directed through a cylindrical lens and through a 2D scanning mirror and a dichroic mirror and a 10× objective 18 lens to shape a circular Gaussian beam into a line shaped pattern and focus it onto the surface of chip 20. A scanning mirror can be programmed to steer the laser beam.

In another embodiment, the source of light patterns is provided by a spatial light modulator. A spatial light modulator can pattern any arbitrary image to be projected onto the photoconductive surface, creating the corresponding virtual electrodes on the OET device. Complex, reconfigurable manipulation patterns can thus be created by simple software programming. The use of an incoherent light source and direct image patterning techniques increases the flexibility and functionalities of OET-DEP sorting platform. For example, in one embodiment, a spatial light modulator consisting of digital micromirror device (DMD) and a 100 W halogen lamp as the incoherent optical source. The typical DMD is a 1024×768 array of individually-addressable micromirrors, each of which is 13.68 µm×13.68 µm. The images displayed on the DMD are controlled via a computer 28. A 10× objective lens 18 can be used to increase the resolution of each DMD mirror to approximately 1.4 µm.

The OET chip 20 is preferably on a stage of microscope 22 that can move two dimensionally and maneuver chip 20 to defined positions. The stage control, microscopic imaging for registering particle (or cell) position and a recorder for collecting data from a microscopic imager may be provided with the personal computer (PC) 28. Computer 28 with software may also used to control the light imaging via laser output control or a spatial modulator as well as to control the signals generated at OET device 20, such as bias voltage from a function generator and microfluidic pump control.

A digital camera 24 connected to the microscope captures the images and displays them upon a color monitor 26 in the embodiment shown in FIG. 1. This allows visualization of cell sorting over time and selection of specific cells for extraction from the chip 20.

Sorting is performed inside a microfluidic chamber 32 of the chip 20 shown in FIG. 1 that is configured with input and output channels and addressable DEP fields. As seen on FIG. 2, the chamber 32 is integrated with one or more microchannels that are connected to input ducts 40 and output ducts 42. The input ducts bring materials to be sorted along with a source of fluid under pressure. The chambers may be arranged in parallel or one chamber 32 can be sectioned off on one chip 30 to increase through put. Chambers 32 can also be arranged in sequence so that separations based on degree of DEP response can take place in stages.

The chip 30 of FIG. 2 preferably has a structure with length 34 and a width 36 and a height 38 that is sized to fit in an XYZ motorized stage of microscope 22. The optional stage is preferably motorized but can be adjusted by hand in one embodiment. The stage may also be moved at different speeds and positions in one embodiment so that the chip moves in relation to the light 52 projected on the chip through lens 18 in FIG. 1.

The stage may also be temperature controlled with heating or cooling elements to provide suitable temperature conditions for sorting live particulates. The stage, optical instrumentation and chip may also be placed in an environmentally controlled sterile environment with respect to temperature, static, humidity, pH, relative pressure and oxygen content etc within an enclosure.

Fluidic input delivery lines 40 are preferably connected to one or more external pumps (not shown) that may be under computer and software control from computer 28 to deliver materials to be sorted and suitable liquid media to the chip 30. Fluid output delivery lines 42 may also be connected to vacuum line to assist with the withdrawal of waste fluids, waste targets, selected targets to reservoirs or other receptacles to facilitate collection and extraction of the desired targets.

FIG. 3 is an example of the general structure of an OET-DEP chip 30 according to the invention. The OET-DEP chip 30 consists of an upper planar electrode 46 of ITO-glass and an opposing lower planar electrode 48 of preferably ITO-glass and a photoconductive layer 50 surrounded by side walls that may include ducts forming chamber 32 that contains a liquid suspension 44.

The upper planar electrode 46 in this embodiment consists of a conductor such as indium-tin-oxide (ITO) which itself is transparent over a transparent glass slide, while the lower photoconductive layer 50 is preferably formed with hydrogenated amorphous silicon (a-Si:H) deposited onto a ITO-coated glass slide 48 via plasma-enhanced chemical vapor deposition (PECVD), however other photoactive materials can also be used. In one embodiment, the lower surface is formed by a 2.5 cm×1.5 cm×1 mm glass slide 48 (other dimensions may also be used), on which is coated a 100- to 200-nm-thick film of indium-tin-oxide (ITO) and a 1-µm-thick film of amorphous silicon (a-Si). The upper surface 46 of the microfluidic chamber is also formed by a glass slide with an indium-tin-oxide film of similar thickness. The two surfaces of the OET microfluidic chamber may be separated by a 100-µm-thick spacer, creating a chamber 32 that can be filled with the fluid suspension 44 of cells/embryos/dielectric particles of interest to be sorted.

An AC bias is placed across the upper electrode and the lower electrode with the photoconductive layer that is preferably under computer and software control.

Projecting light patterns 52 on the lower photosensitive electrode 48 modifies the electric field profile creating electric field gradients near the illuminated areas and a dielectrophoretic force. Focusing light patterns on a photoconductive portion of the top 46 or bottom 48 electrode surfaces to induce a local electric field creates a "virtual electrode" that is configured in time and location for dielectrophoretically attracting or repelling cellular objects or other particles in response to the light pattern. The position and timing of the light patterns can be determined dynamically in response to feedback received from registering the position and DEP response of particles or cells confined within the chamber 32.

The light patterns 52 can also vary in size and shape and intensity allowing modulation of characteristics of the resulting DEP fields and therefore the forces experienced by cells or particulates within the chamber. Patterns with one portion that has a different intensity than another can also be produced. Accordingly, the pattern generator can provide designed patterns in selected shapes locations and times. Sophisticated virtual electrodes with optimized field strengths can be easily patterned and reconfigured to create dynamic electric field distributions for continuous particle manipulation with or without the assistance of fluidic flow.

Dielectrophoretic force is also AC frequency-dependent. Thus, by varying the frequency of the applied AC bias, the force can be adjusted from an attractive force to a repulsive force, or vice-versa. Since OET uses optically-induced DEP, the OET force is also tunable in the same manner. As a result, there are two operating modes for OET: positive OET, in which cells and microparticles are attracted to the illuminated areas, and negative OET, in which cells and microparticles are repelled by the illuminated areas.

Computer software or operator commands can provide control signals for sequentially directing light patterns 52 and can move particles that have been attracted to the electrode through selected positions and structures within the chamber 32 or associated fluidic structures of chip 30. By programming the projected optical patterns, field intensities and chip positions, multi-step diagnostic protocols can be achieved by combining multiple functions such as transporting, sorting, recycling, and separating in space and time.

Figure 4:
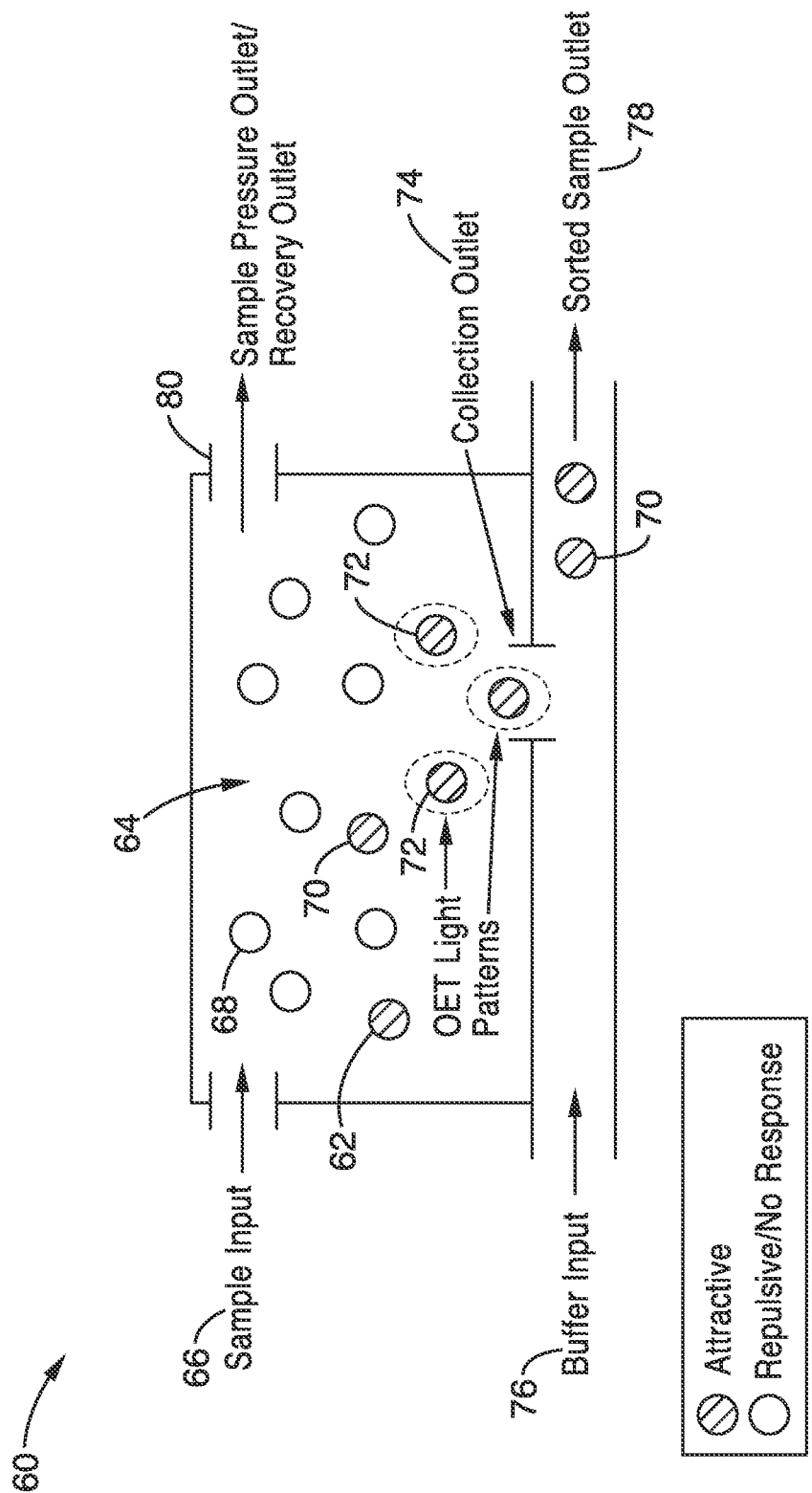
FIG. 4 is a schematic top view of an OET-DEP chip embodiment using active particle trapping and movement.

Referring now to FIG. 4 through FIG. 8, several embodiments of cell sorting platforms are schematically shown that may be adapted to provide different sorting needs. FIG. 4 is a schematic top view of an OET-DEP chip embodiment using active particle trapping and movement. This embodiment 60 of the device is designed to perform active sorting of cells or particles that are attracted to the light actuated DEP electrode and then directing the trapped cells to an outlet flow for collection. In this embodiment, a sample chamber 64 has bottom floor 62 with a layer of amorphous silicon that is configured to be exposed to light patterns that create virtual electrodes as seen in FIG. 3. The sample chamber 64 is filled with the cells to be sorted. The heterogeneous cell solution may be injected directly into the chamber through the inlet 66 or enter from a microfluidic channel connected to the inlet 66. In the illustration shown in FIG. 4, the solution has cells 68 that are repulsed or have no response to a DEP field and cells 70 that are attracted to a DEP field. A light pattern 72 is generated to manipulate the cells of interest using OET-induced DEP force.

Although the cells 70 of interest are those with an attractive response to OET light patterns are shown, the light patterns can be reconfigured to manipulate cells with a repulsive response to OET, or cells with another distinguishing characteristic, such as the expression of a fluorescent marker or other label as well.

The cells of interest 70 are individually guided in parallel by OET light patterns 72 from the sample sorting chamber 64 to a collection outlet 74 and into a microchannel 76 output that terminates in the collection unit 78. A buffer solution flows, at a slow rate (or it can be pulsed-flushed) through the microchannel 76, so once the cells enter this flow, they are flushed to the output 78 where they can be collected. Accordingly, specific cells or groups of cells can be separated and transferred to an output microchannel 76 and collected.

To prevent unsorted cells from entering the collection micro-channel outlet 74 due to increased pressure within the sorting chamber 64 as it is filled, an outlet 80 allows cell solution to drain out of the chamber as the chamber is filled. This outlet 80 can also be used to recover excess sample or separated cells 68 that are concentrated by the removal of the cells of interest 70 over time.

Figure 5:
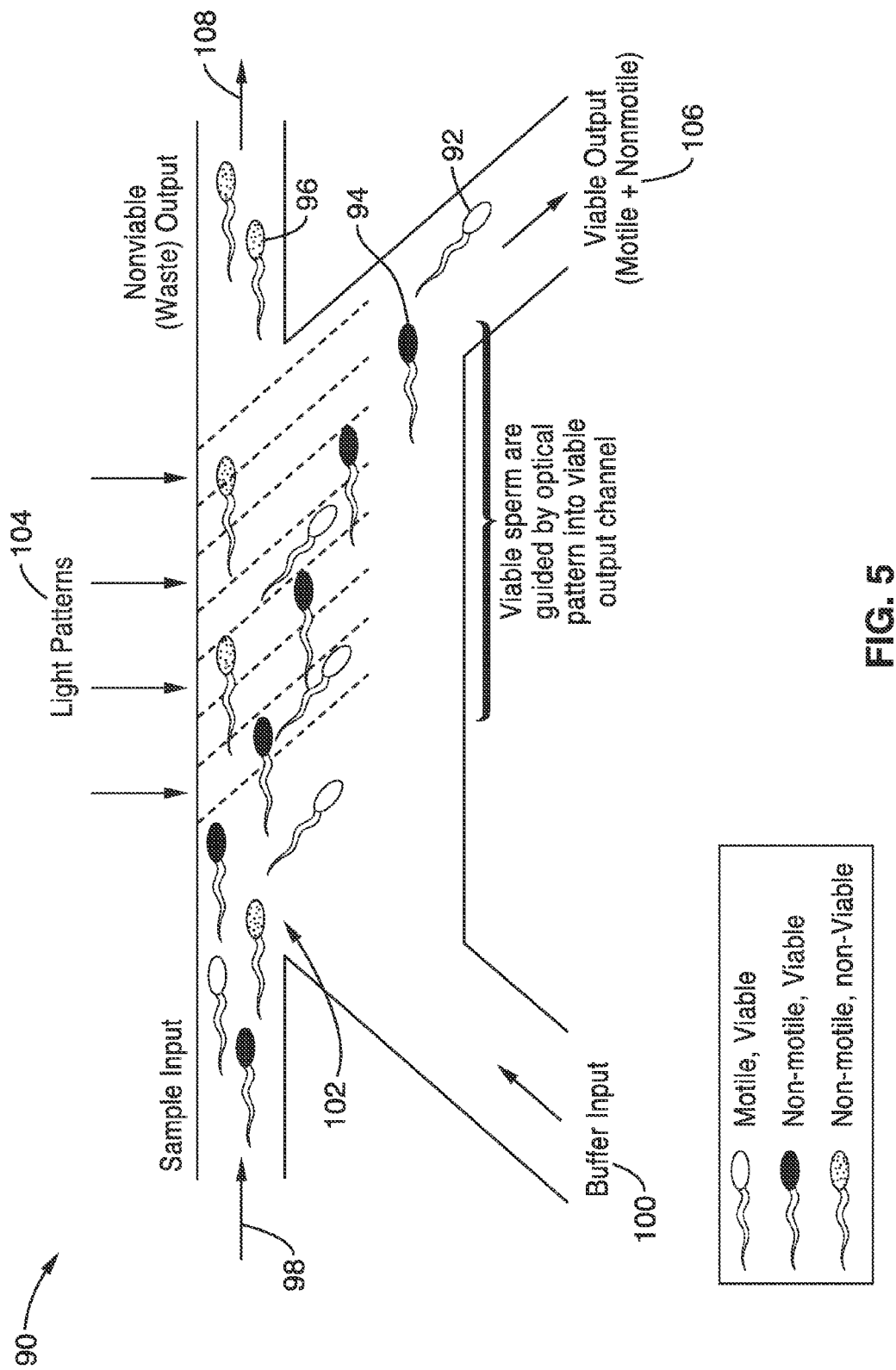
FIG. 5 is a schematic top view of an alternative embodiment of an OET-DEP chip using active and passive particle sorting.

FIG. 5 is a schematic top view of an alternative embodiment of an OET-DEP chip using active and passive particle sorting to illustrate one separation scheme for the separation of sperm. The sorting device 90 performs the passive sorting of motile sperm 92 in parallel with the active sorting of viable non-motile sperm 94 from non-viable motile and non-viable non-motile sperm 96.

In the embodiment 90 of FIG. 5, the sperm sample, consisting of a mixture of viable sperm and non-viable sperm, flows into the sorting device through a microfabricated channel 98. A second buffer solution flows through a separate input channel 100. The flows of the sample input channel and buffer input channel join together in the sorting area but the two liquids do not mix together due to laminar flow in the microfabricated device. Motile sperm are able to swim from the sample input flow to the buffer flow under their own power across the interface 102 between the two flows, which is the passive sorting functionality of the sorting device 90. The non-motile viable sperm 94 are also introduced to the buffer flow across the interface 102 using dielectrophoretic (DEP) force. This force is generated using light patterns 104 to form a virtual electrode and the DEP attractive force. Non-motile but viable sperm 94 will be attracted to and trapped by the light patterned electrode (along with motile sperm) and will be introduced into the buffer flow from the buffer input 100. Alternatively, the appropriate DEP force can be generated using microfabricated electrodes. The DEP force produces an attractive force on the viable non-motile sperm, pulling them into the buffer flow. Thus, the buffer output channel 106 will contain only viable motile and non-motile sperm. Non-viable non-motile sperm 96 are not attracted by DEP force and will remain in the sample channel flow, which goes to the waste output 108.

In an alternative design, the light-patterns can continuously move across the sample input channel in the oblique direction shown in FIG. 5 to the buffer flow across the interface 102. When each light pattern reaches into the buffer flow area, either the entire OET light area turns off or the sample input side of the light bar remains on while the buffer side turns off to release any cells that remain and are not removed by the forces of the fluid flow from the buffer flow.

Accordingly, non-motile but viable sperm can be separated and utilized for fertilization along with viable motile sperm. Non-viable motile and non-motile sperm will be directed to the waste output 108.

Figure 6:
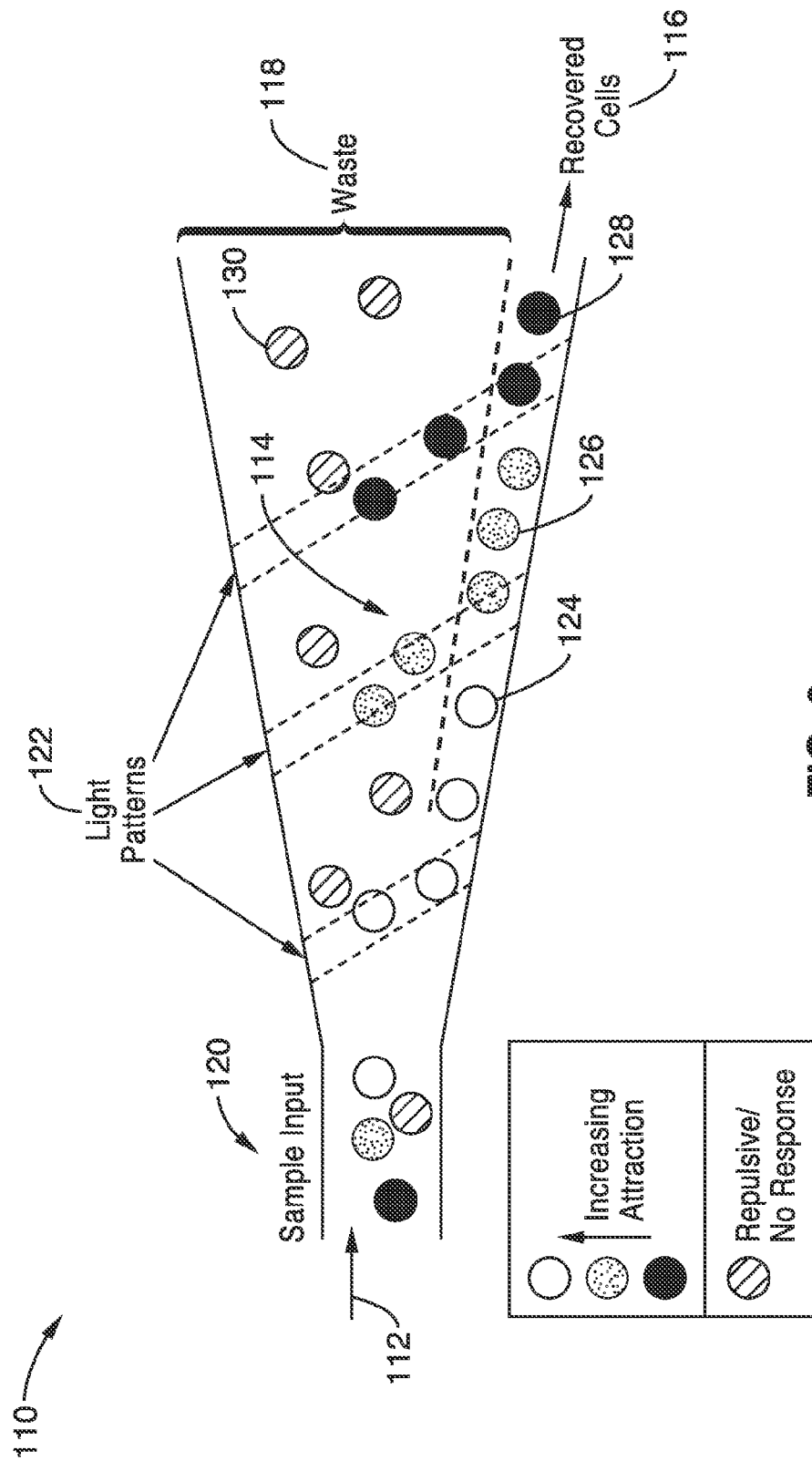
FIG. 6 is a schematic top view of a second alternative embodiment of an OET-DEP chip for high through put separations.

FIG. 6 is a schematic top view of another alternative embodiment of an OET-DEP chip for use with high throughput separations. The sorting device 110 is designed to maximize the recovery of cells with a positive response to OET manipulation. The samples can contain a mixture of different cell types, and/or cells of with different magnitudes of positive OET-DEP response.

The device 110 has an input microchannel 112 that widens into a sorting area 114 and a flow of buffer is maintained through the channel and sorting area. There is also an exit port or channel 116 to recover the separated cells and a waste port 118 to receive the waste cells 130. Several separation structures can be joined in series to facilitate the separation of larger volumes and numbers of cells.

A sample mixture of cells 120 is introduced into the input microchannel 112. In the sorting area 114, the channel width is increased resulting in a flared microchannel in the embodiment shown. This change in dimension causes the velocity of the fluid flow within the area of increased diameter to decrease as the channel width increases. Light patterns producing electrodes 122 span the sorting area 114, attracting cells and guiding them to one side of the channel for recovery using DEP force. The cells 124 that have the strongest attractive response to DEP will be trapped and guided by the first light patterned electrodes. However, cells 126 and 128 that have weaker attractive responses will flow past the initial OET manipulation patterns 122 at a relatively high velocity from the flow and a cell's weak DEP response may be insufficient to allow it to be caught and shifted downward by the early light pattern created electrodes. However, as the channel 114 becomes wider and the flow speed of the buffer and cells decreases the subsequent manipulation patterns 122 will be sufficient to guide any cells 126 and 128 with relatively weaker attractive force towards the recovery side of the channel to the collection port 116. Thus, all cells with any degree of attractive response can be recovered using this sorting device. All recovered cells exit the sorting chip via an output that is separate from the waste output. In this way, a single solution of cells is separated into two, with one containing the desired cells, and the other containing waste. In addition, the cells 124, 126 and 128 can be eluted from the device based on the degree of DEP attraction and manipulation of the patterns 122 over time.

Figure 7:
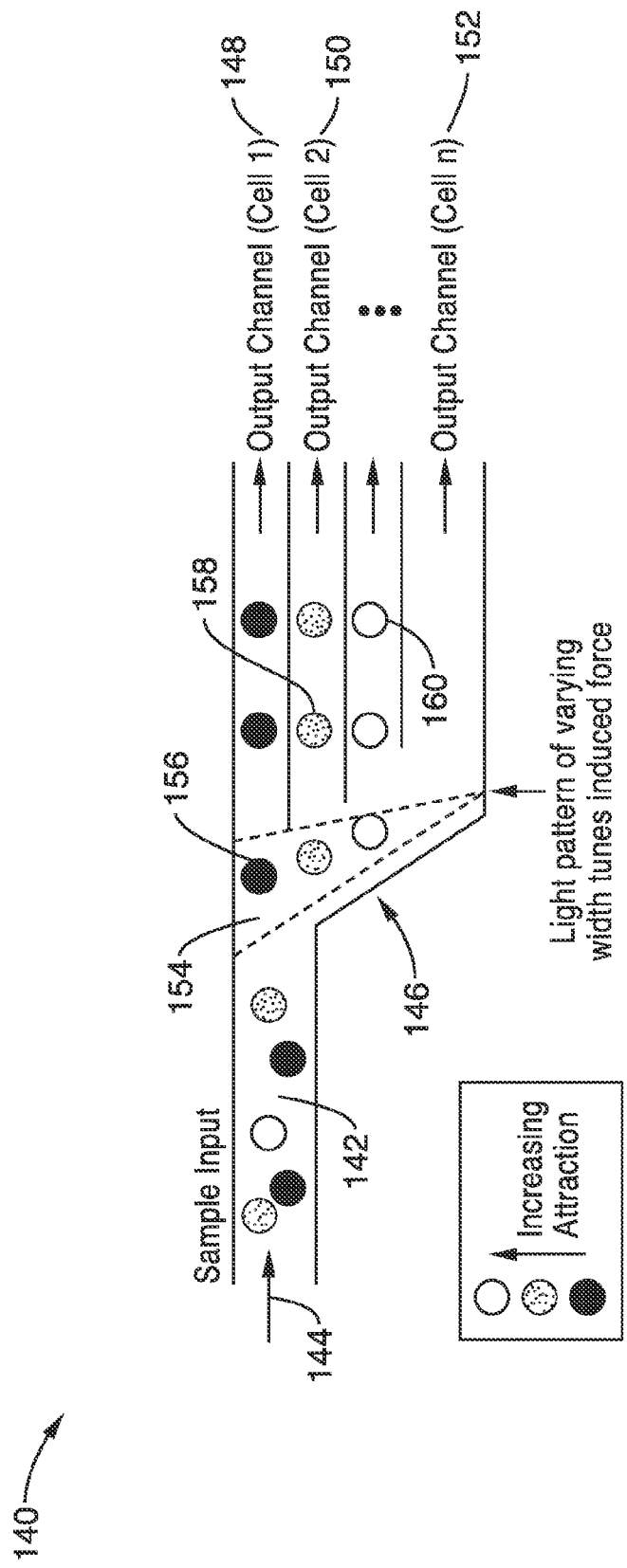
FIG. 7 is a schematic top view of a third alternative embodiment of an OET-DEP chip for high through put separations with multiple output channels.

FIG. 7 is a schematic top view of another embodiment 140 of an OET-DEP chip for high through put separations with multiple output channels. The device 140 is designed to perform active sorting of multiple different cell types or cells of different relative viability.

A mixed sample 142 is introduced into the input microchannel 144 that also contains a continuous flow of buffer. The sample 142 can be pre-filtered to remove dead cells by filtering before running the sample through the sorting device 140. In another embodiment, different separator types are coupled in sequence. For example, the sorting device shown in FIG. 6 can be used as a first-stage sorter that removes dead cells and outputs live cells, which are then sorted by the sorting device of FIG. 7.

The sample input channel 144 flares outward to form a sorting area 146 and breaks up into a number of different output channels 148, 150 and 152. At least one light pattern 154 of varying widths spans the sorting area 146 in front of the output channels 148, 150 and 152. As the width of the light patterned electrode 154 decreases, the OET-induced DEP force produced by the electrode will also decrease. Therefore, cells 156 with the least attractive force will not move downward along the light pattern, but will instead end-up in the first output channel 148. In other words, the left to rightward trajectory of cells with a weakly positive OET-DEP response will be distorted the least.

Furthermore, cells 158 and 160 with increasing attractive force, upon being trapped within the light-pattern, will migrate downward, along the light pattern, until the OET-DEP induced force is less than the net force from the microfluidic flow. At this point, the cells will no longer be trapped by the light patterned electrode 154, and will flow directly into the corresponding output channel 150 and 152. In this manner, cells can be separated into subpopulations based on their OET-DEP induced force. Output channels can be connected to a storage reservoir or to a flexible plastic tubing in order to transport the cells into the desired receptacle or solution outside of the chip 140.

Figure 8:
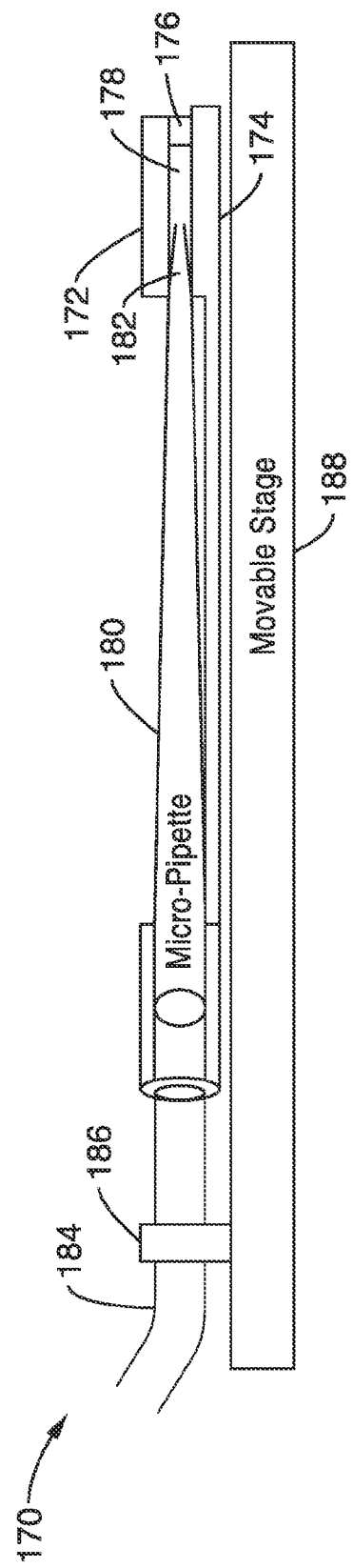
FIG. 8 is a schematic side cross-sectional view of a fourth embodiment of an OET-DEP chip including a micropipette for removal and isolation of specific particles.

FIG. 8 is a schematic side cross-sectional view of another embodiment of an OET-DEP chip 170 including a micropipette for removal and isolation of specific particles. The chip 170 includes a top plate 172 and a bottom plate 172 separated by a spacer 176 to form a microchamber 178. The space between the two plates 172 and 174 preferably measures between 100 micrometers and 200 micrometers. The microchamber receives the cell targets suspended in minimally-conductive medium for separation with the OET-DEP fields. The top plate 172 is preferably ITO coated glass and the bottom plate ITO coated glass with a coating of amorphous silicon and electrical connections to provide the OET-DEP fields when exposed to light patterns.

The lower plate 174 is much larger than the top plate 172 to accommodate the placement of the tip 182 of a micropipette 180 in the microchamber 178. The proximal end of the micropipette 180 is coupled to an optional source of suction through a tube 184. Gentle aspiration can be applied to the micropipette 180, in order to aspirate the desired target into the tip 182 of the micropipette that has been collected. Once the target is inside the micropipette tip 182, the micropipette 180 can be withdrawn, and the individual target can be retrieved from the micropipette 180 simply by the reverse process: positive pressure is applied to the micropipette (from the opposite end, towards the tip).

Alternatively, a plurality of micropipette tips could be interposed between the upper 172 and lower 174 microchamber plates, such that one micropipette 180 can deliver an inflow of fluid and/or fresh target, while other micropipettes can be used to retrieve target. Furthermore, aspiration into or out of (any) micropipette tip located within the microchamber can be performed under direct vision, thus increasing the potential for selectivity.

The chip 170 is preferably placed on a movable stage 188 and the tube is optionally mounted to the stage with a fastener 186. Light patterns are directed through the stage 188 and the location of the pattern on the chip 170 is determined by the movement of the stage 188.

In one embodiment, the lower plate 174 has a channel underneath the body of the pipette 180 to reduce shear forces with the placement or removal of the tip 182 within the microchamber 178.

This embodiment may be particularly suitable for identifying and retrieving specific individual cells or groups of cells that have been sorted by the apparatus. It should be noted that retrieval of all of the sorted targets from the OET chip ("non-specific retrieval") for an assay is, for some applications, sub-optimal, because it does not preserve the sorting order achieved during OET sorting process. Nor does it allow the user to identify which individual target corresponds to which OET assay data result since all of the targets become "mixed" with "non-specific" retrieval.

With the embodiment shown in FIG. 8, for example, it is possible to obtain an OET-DEP assay of individual targets and to measure and index the OET response of each target. The individual targets can be segregated (in any spatial order desired) and selected on the basis of their OET assay response, from the rest of the targets within the OET sorting field.

The segregated individual targets can then be retrieved by micropipette aspiration, where the chosen target is guided to the micropipette tip 182 by OET and then drawn into the micropipette 180. The micropipette 180 can then be removed from the OET chip, and, the target can be transferred to a separate receptacle, for clinical or investigational use. For example, if the target is a sperm cell, the OET-assayed sperm can then be injected into an oocyte (egg), as part of IVF/ICSI (intracytoplasmic sperm injection). While there is certainly clinical benefit from diagnostic assay for sperm, embryos, stem cells, etc., the primary clinical utility (in the field of reproductive medicine) comes from not only being able to assay the targets but also to be able to selectively retrieve individual targets after the assay.

Figure 9:
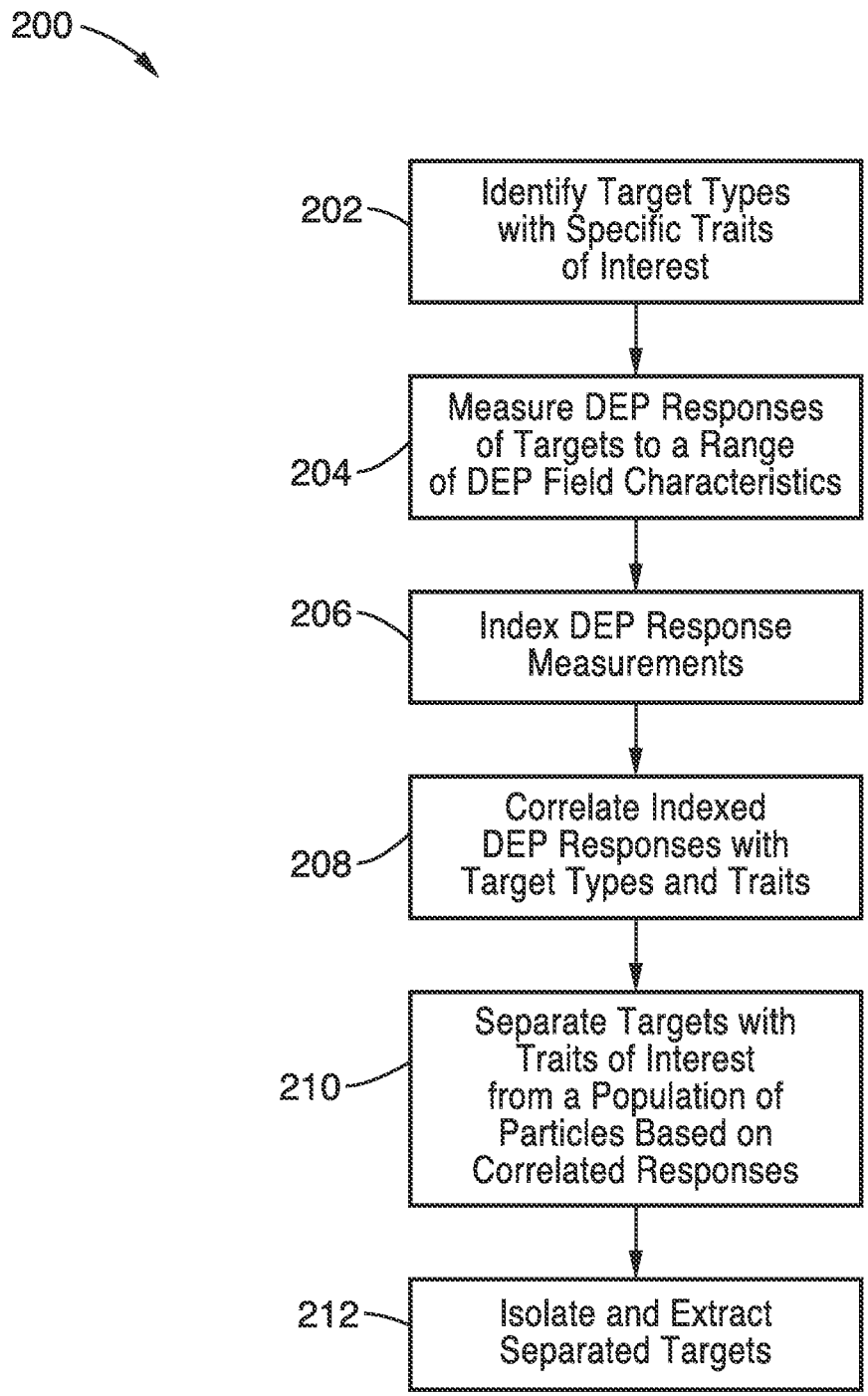
FIG. 9 is a flow diagram of a method for separation of particles with identified traits based on DEP responses.

Turning now to FIG. 9, one method 200 for separating cells according to identifiable traits is generally shown. In this embodiment of the method, potential target cells or other particles with specific traits are identified and isolated at block 202. Traits may include a morphological or genetic defects, health, viability, physiological state, suitability for a particular purpose, membrane properties (permeability, capacitance, and conductivity), internal conductivity, chromosome content, such as chromosome number, degree of chromosome damage, chromosome type (gamete sex-sorting), and characteristic genetic aberrations of known and unknown diseases and other identifiable traits of interest.

For example, during work with human sperm samples while attempting to sort live from dead sperm it was discovered that among "live" sperm, there was a significant range in the magnitude of positive response that "live" cells exhibited towards DEP. This was a key observation, and suggested that DEP was capable of sorting sperm not only on the basis of their absolute response (index of absolute viability), but also on the basis of their relative response to DEP (index of relative viability). Sperm health was a continuous variable rather than binary suggesting that DEP is capable of identifying which specific sperm (or any other cell type) is relatively more or less healthy that the other viable cells. This ability to substratify sperm (or any other cell type) based on relative viability, can be used to guide selection of only the healthiest sperm, eggs, and even embryos, for artificial reproduction procedures.

As embryos age (1-cell to 2-cell to 4-cell . . . ) the DEP response of the embryo progresses from positive (attractive) to negative (repulsive). This gradation in response allows the accurate and systematic assessment of the morphological state of the embryos. Based on the comparison of early blastocyst embryos (the most common developmental stage at which embryos are transferred in human IVF) it is clear that the OET-DEP assay could guide embryo selection based on the magnitude of the negative DEP response for more developmentally mature target embryos and also guide the exclusion of the positive DEP response for less mature embryos. Furthermore, the most mature target embryos could be individually selected among a cohort of otherwise indistinguishable embryos based on response since it is assumed that the faster developing embryos are likely to be the most viable upon implantation. Similar to previous findings with sperm, completely dead and partially degenerating embryos, responded minimally to the OET DEP patterns. Accordingly, it was seen that a characteristic DEP response of cells with identified traits could be correlated with those specific traits of interest.

The selected cell types with the trait or traits of interest that are identified and obtained for analysis at Block 202 are exposed to a range of DEP field characteristics such as field intensity and frequency and the response of the selected cell types to the range of DEP field characteristics is measured at Block 204. Measurements may include velocity of cells attracted to the electrode or the strength, relative strength of attraction to an electrode within a fluid flow, and direct measurement of the Clausius-Mossotti (CM) factors.

It has been observed that the dielectric potential of any cell depends on its physiologic status, composition, morphology and phenotype in addition to the frequency of the applied electrical field. Therefore, the same cell type in different physiological states or with other different traits may possess distinctly different dielectric potentials, which in turn can be utilized for separation.

The response of an object, such as a cell, to a DEP field may be characterized by the real part of the Clausius-Mossotti (CM) factor. This is an effective electrical polarizability of the object relative to that of the surrounding medium. The CM factor takes into account all of the physical properties of the object and media. This CM factor can either be positive or negative in value (attractive or repulsive forces) depending on the relative admittances of the particle (cell) and media. Cells in different physiologic states possess distinctly different electrical properties, resulting in different DEP responses.

At Block 206, the DEP response measurements for the target types in a range of different DEP fields are indexed and recorded. A reference library of types and DEP responses can be assembled. Correlations between indexed DEP responses and conditions with target cell types and cell traits can be made and optimum conditions for the strongest attractive or repulsive responses can be determined at Block 208.

At Block 210, the indexed responses and information gathered at Block 208 can be used to establish the sorting conditions for sorting a heterogeneous population of particles for the target particles with traits of interest from the other particles that may have similar features. Optimum sorting conditions will allow the exclusion of cells with response magnitudes below or above the indexed response range. In other settings, the indexed responses will indicate that the strongest response to the DEP field represents the trait and the separation criteria.

While a diagnostic assay for sperm, embryos, stem cells, etc. is certainly of benefit, the primary clinical utility in the field of reproductive medicine, comes from being able to both assay the targets and then to be able to selectively retrieve individual targets after the assay. Therefore, specific targets or groups of targets are extracted at Block 212.

In addition, for some applications retrieving all or most of the targets loaded onto the DEP chip ("non-specific retrieval") for assay is not desirable because it does not preserve sorting order achieved during DEP sorting, nor, does it allow to allow the user to identify which individual target corresponds to which DEP assay data result since the targets become "mixed" with "non-specific" retrieval. One embodiment allows selection and extraction of specific individual targets according to their DEP responses.

One illustration of this need is in reproductive medicine and isolation of healthiest eggs or sperm for use with established fertilization procedures. In this case a semen sample of a large population of cells is assayed to identify which among the sample are the most viable.

Once individual sperm that meet selection criteria are found within the sample with the DEP separation, it is desirable to be able to retrieve just these sperm, so that, afterwards, the operator is provided with individually segregated sperm, for which the OET response is known (for each sperm).

The operator knows which of the sorted sperm had the "best" DEP response during assay, and which one had the second best response, etc. The relative magnitude of a sperm's response to OET DEP is itself an index measure of the sperm's relative viability. These sperm, stratified now by DEP response can then be retrieved and used, in a preferential order, to fertilize oocytes (eggs) to make embryos. Among the resulting embryos, which embryo was made from which individual sperm, is known.

Similarly, the methods can be used in the selection of the most suitable embryos for use in established artificial fertility procedures. One major factor involved in successful in-vitro fertilization (IVF) procedures is the selection of healthy embryos for implantation in the patient. The primary indicator of a healthy embryo is its ability to develop at a faster rate relative to its peers. Currently embryos are selected by an experienced technician who selects based on observation. The present invention provides a method with a qualitative determination of which embryo reaches certain developmental stages faster than others and are the best candidates for successful implantation.

The current low success rate (defined as live births per number of embryos transferred), high risk of morbidity and mortality (health risk to mother and fetus), and the high cost of IVF could all be improved significantly with the use of the present invention that allows one to reliably predict the viability of each individual embryo prior to transfer. This makes it possible to transfer only the healthiest and fewest number of embryos (ideally only one) thereby reducing the rate of multiple births without reducing pregnancy rates.

It is anticipated that the ability to non-invasively distinguish between the healthier embryos before transfer so that only the healthiest embryos are actually transferred as well as identifying and using the healthiest sperm will substantially improve the rate of successful implantation of embryos from current levels that range from 8 to 25 percent to success rates preferably between 30 to 40 percent, and more preferably between 40 and 50 percent, and optimally between 50 and 60 percent.

It will also be seen that the present invention can provide an assay that could determine whether gametes from a person with Cystic Fibrosis (or other heritable diseases with incomplete penetrance) carries the mutation, for example. The methods could be used, for example, to screen the sperm, oocytes, or embryos of a couple, each of whom is heterozygous for the mutation (and thus is un-affected), to prevent from joining, during IVF or IVF/ICSI gametes that either carries the mutation, or, to embryos that are hetero or homozygous for the mutation.

Figure 10:
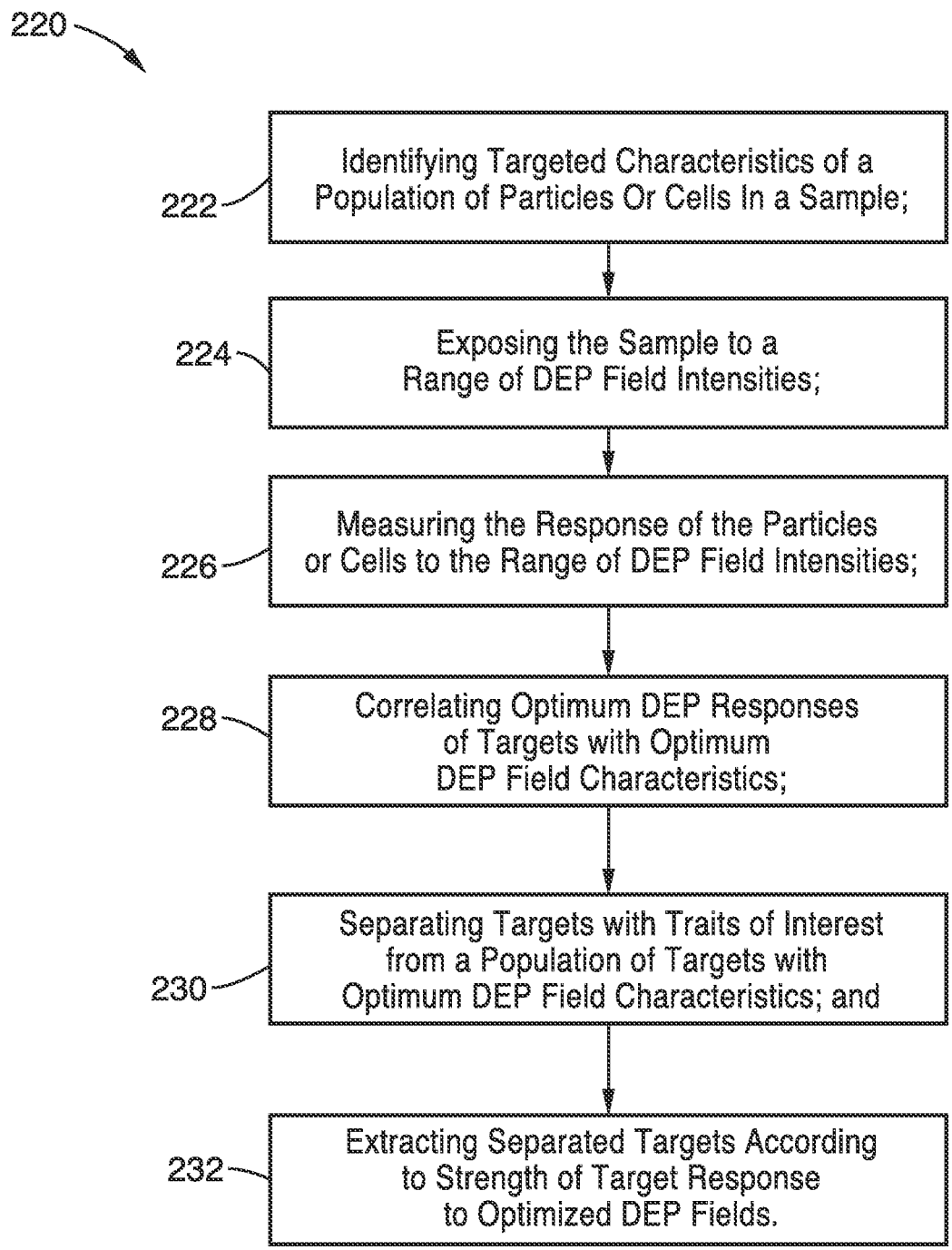
FIG. 10 is a flow diagram for an alternative method for separation of particles according to the invention.

Turning now to FIG. 10, an alternative embodiment 220 of the method is shown that utilized known optimum DEP filed characteristics and established DEP responses that can be referenced. At Block 222, targeted characteristics of a population of particles or cells in a sample are identified and the sample population is exposed to a range of one or more DEP field intensities at Block 224, preferably using an optimum DEP field.

At Block 226, the responses of the particles or cells to the DEP field may be measured and correlated to the optimum DEP responses of targets with optimum DEP field characteristics at Block 228. The correlated responses of the cells to the DEP field permits the separation of targets with traits of interest from a population of targets with optimum DEP field characteristics at Block 230 and the separated targets according to strength or magnitude of target responses to the optimized DEP fields can be extracted at Block 232.

Figure 11:
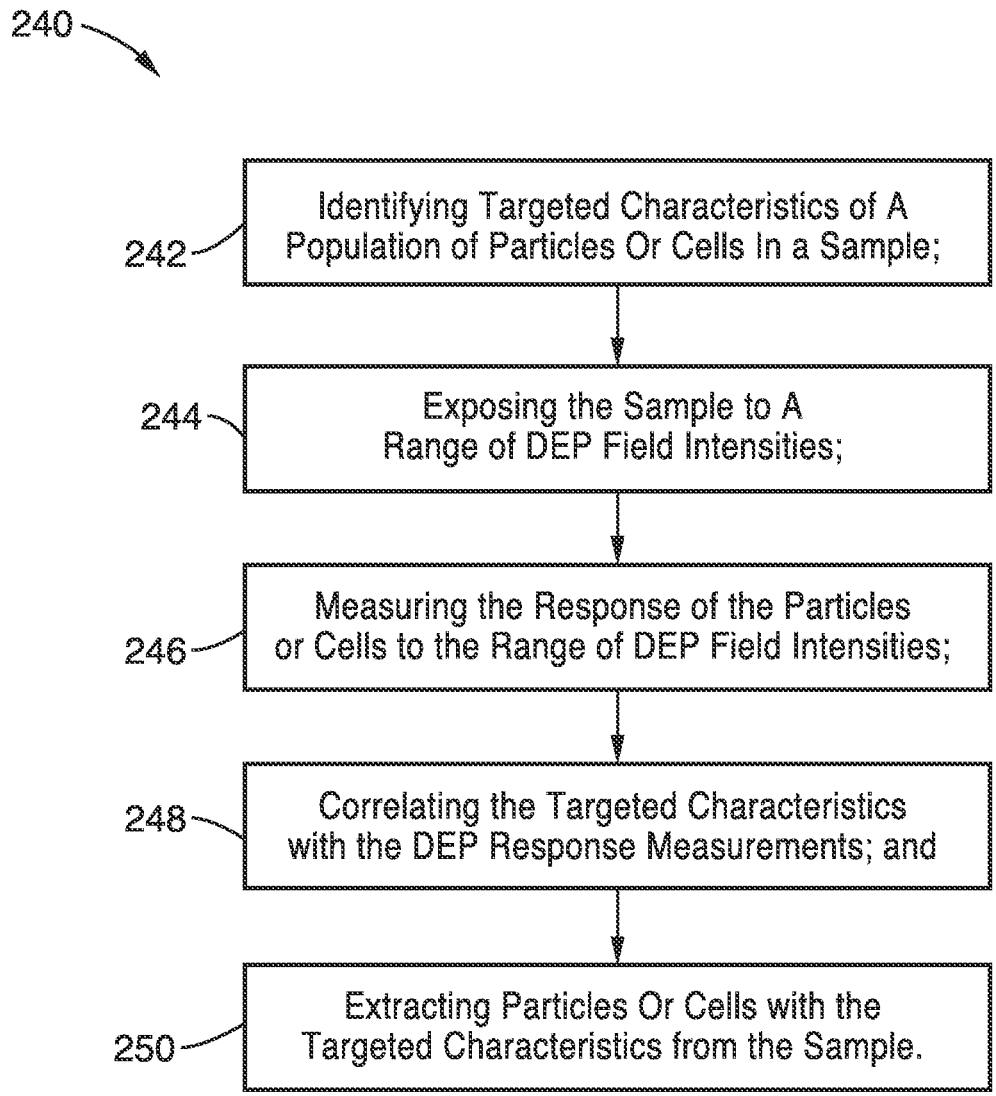
FIG. 11 is a flow diagram for an alternative method for separation of particles according to the invention

It can be seen that sorting characteristics for a particular trait from a population of cells can be determined directly with comparisons to cells without the trait or by reference to an established library of sorting characteristics. In the embodiment 240 in FIG. 11, targeted characteristics are identified for sorting at Block 242 of a population of particles or cells in a sample. At Block 244 the sample is exposed to a range of DEP field intensities. The response of the particles or cells to exposure the range of DEP field intensities is measured at Block 246 and the targeted characteristics are correlated with the DEP response measurements at Block 248. The differences in the relative response to the DEP fields will permit the characterization of targeted response and separation of the targets from the population based on the DEP response. The separated particles or cells with the targeted characteristics from the sample can be accomplished at Block 250.

As an illustration, OEP-DEP was used to sort adipose tissue derived multi-potent mesenchymal cells commonly referred to as "adipose tissue derived (adult) stem cells" (ADSC). While investigating how ADSC could be used as a source of cellular therapy to treat urologic diseases, it was observed that when ADSC cells are processed from the adipose tissue where they reside, the chemicals and mechanical digestion process causes 15-20% of the ADSC to die, and a significant portion of the remaining live ones, to be damaged. The goal was to determine whether "live" ADSC could be separated from the "dead" and damaged ADSC fraction, so that when acquired ADSC cells are injected into the body for treatment, only the healthy, live ADSC would be introduced into the patient rather than dead or damaged cells.

Using a population of ADSC stained with Trypan Blue and Calcein dyes (two standard "viability" assays that stains dead cells blue, while live cells exclude the dye and remain unstained), it was shown that cells that stained blue from the Trypan Blue dye responded negatively (were repulsed) to OET DEP, while cells that excluded the Trypan Blue dye responded positively (with attraction) to OET-DEP fields.

Accordingly, the present invention provides a non-invasive separation apparatus and method that separation and extraction of target cells and does not compromise the vitality of living particulates.

The invention may be better understood with reference to the accompanying examples, which are intended for purposes of illustration only and should not be construed as in any sense limiting the scope of the present invention as defined in the claims appended hereto.

Example 1

Using a hybrid inbred mouse model and the OET apparatus, in a 2-phase blinded study, it was first determined how embryos that were cultured in an optimized culture medium (KSOM+AA) responded to OET-DEP at varying stages of development (1-cell, 2-cell, 4-to-16-cell/morula, and, early and late blastocyst stages). Next, to assess whether this technique could be used to guide embryo selection, responses from embryos cultured in KSOM+AA were compared with morphologically identical embryos cultured in a sub-optimal medium (M16). In-vitro culture in M16 yields, at all pre-implantation stages of development, a subset of embryos that are indistinguishable from ones cultured in KSOM+AA. However, M16 has been shown to sub-optimally sustain in-vitro embryo development, as compared to KSOM+AA, at all stages of development. This difference in quality between the two media is magnified as cultured embryos progress to later stages of development in-vitro. Finally, as a preliminary effort to assess the safety of OET for embryos, the survival and continued in-vitro development of embryos following OET assay was analyzed.

In order to demonstrate the apparatus and methods for the separation of embryos, a 6" glass wafer with a 300 nm layer of sputtered indium tin oxide (ITO) was coated with a 1 μm layer of hydrogenated amorphous silicon (a-Si:H) deposited via plasma-enhanced chemical vapor deposition (PECVD) (100 sccm 10% $SiH_4$:Ar, 400 sccm Ar, 900 mTorr, 350° C., 200 W). The a-Si:H coated ITO wafer, along with another 6" ITO-coated glass wafer, was then diced into 2×2 cm chips with a dicing saw forming the bottom and top OET substrates, respectively. The bottom OET substrate (a-Si:H coated ITO) was then subjected to a brief oxygen plasma (51.1 sccm $O_2$, 300 W, 1 min.) and placed in a solution of 2-[Methoxy(polyethyleneoxy)propyl]trimethoxysilane for 2 hours. The immersed chips were then rinsed in ethanol and air dried. This resulted in a thin layer of poly-ethylene glycol (PEG) on the surface of the bottom substrate which aided in reducing adherence of the embryos to the surface. Electrical contacts were made to the ITO on both the top and bottom substrate using an electrically conductive silver epoxy.\

A custom-built microscope was assembled and used for all experiments. The sample was placed on an XYZ micro manipulator connected to a mechanical stage drive, which allowed the stage to be moved at a known rate. Viewing occurred from the topside via a 5× objective lens. Brightfield Köhler illumination was provided via a fiber illuminator coupled through a 50/50 beam splitter. The optical patterns used for manipulation were formed using a commercial data projector controlled by an external computer running commercial presentation software. The images were focused onto the substrate by means of a telescope and long-pass dichoric mirror. Viewing and image capture occurred via a CCD camera connected to an external computer. Electrical bias was applied using a standard function generator.

The DEP response and maximal DEP-induced velocity of the subject embryos was measured by projecting a rectangular light pattern onto the chip substrate. The light pattern was positioned such that the leading edge of the light pattern was coincident with the outer edge of the embryo. The stage was then translated at varying speeds to extract the maximum speed at which the embryo could be moved by the adjacent light pattern. A positive dielectrophoretic (pDEP) response was defined when the embryo was attracted towards the center of the light pattern when the light pattern was brought near the embryo. The fastest pDEP speed was defined as the maximum stage speed (light pattern) at which the embryo could still stay within the confines of the light pattern (i.e. the minimum speed at which the light pattern could no longer trap the embryo). The pDEP speeds were annotated as a positive number. A negative dielectrophoretic (nDEP) response was recorded when the embryo was repulsed away from the edge of the light pattern when the light pattern was brought near the embryo. The fastest nDEP speed was determined by finding the maximum stage (light pattern) speed at which the embryo could still stay outside the perimeter of the light pattern. The nDEP speeds were annotated as a negative number.

A total of 410 zygotes were harvested at the 1-cell stage and were divided equally into groups cultured in KSOM+AA and M16 medium. Ovulation had been induced by administering 5 IU PMS (IP) followed 48 hrs later by 5 IU HCG (IP) to 20 C57BL6×DB2 F1 3-4 week old females. Females were then mated to 5 month old Male C57Bl6 mice. Embryos that failed to progress to the 2-cell stage, or appeared developmentally delayed by >24 hours at time evaluation of were removed from the culture dish and excluded from analysis.

At 1-cell, 2-cell, 4-16 cell, early blastocyst and late blastocyst stages, cohorts of 29-43 embryos were taken from their respective culture medium, suspended in a low conductivity media (EP), and then underwent the OET assay. The number of hours post fertilization that the embryo cohorts were assayed at each developmental group was tabulated. M16 cultured embryos generally required 6-12 hours of additional time in culture to reach equivalent late developmental stages, as embryos cultured in KSOM+AA.

Maximum induced velocity was measured. The top OET-DEP substrate of the device was placed on top of the solution containing the embryos and separated from the bottom substrate by a 200 μm spacer. The device, now containing the embryos, was placed upon the manipulation stage and electrical bias was applied (20 Vppk, 100 kHz). The DEP response and maximal DEP-induced velocity was then measured by projecting a rectangular light pattern onto the substrate. The light pattern was positioned such that the leading edge of the light pattern was coincident with the outer edge of the embryo. The stage was then translated at varying speeds to extract the maximum speed at which the embryo could be moved by the adjacent light pattern. A positive dielectrophoretic (pDEP) response was defined when the embryo was attracted towards the center of the light pattern when the light pattern was brought near the embryo. The fastest pDEP speed was defined as the maximum stage speed (light pattern) at which the embryo could still stay within the confines of the light pattern (i.e. the minimum speed at which the light pattern could no longer trap the embryo). pDEP speeds are annotated as a positive number. A negative dielectrophoretic (nDEP) response was recorded when the embryo was repulsed away from the edge of the light pattern when the light pattern was brought near the embryo. The fastest nDEP speed was determined by finding the maximum stage (light pattern) speed at which the embryo could still stay outside the perimeter of the light pattern. nDEP speeds are annotated as a negative number.

All embryos from both the KSOM+AA and M16 groups assayed at the 1-cell, 2-cell, and 4-16 cell/morula stages exhibited a positive DEP response (pDEP) to the assay OET field (attraction to the light pattern). Among early blastocysts, the majority of embryos cultured in either media exhibited a negative DEP (nDEP) response (i.e. repulsion from the light pattern). All late blastocyst and hatching embryos cultured in either medium also showed an nDEP response. Late blastocysts, and in particular, those that were partially hatched, were generally too adherent to the OET substrate to allow them to be moved long distances by the OET field. Thus, a reliable maximum OET-induced velocity could not be calculated for these groups, and they were excluded from further analysis.

Several trends were evident from the velocity data collected at each stage. For KSOM+AA embryos, the mean maximum induced velocity significantly decreased (became less positive) between each successive stage of development ($p<0.006$). Likewise, for M16 embryos, the mean maximum induced velocity also decreased significantly ($p<0.0001$) at each successive stage of development.

Second, there were significant differences in mean OET-induced velocity between comparable KSOM+AA and M16 matched-pair groups. Among matched cohorts (morphologically indistinguishable embryos grown in either KSOM+AA or M16) at the 1-cell, 2-cell, and early blastocysts stages, those cultured in KSOM+AA exhibited a significantly less positive/more negative response to OET as compared to those from the M16 group.

The group containing a mixture of 4-16-cell stage embryos were excluded from analysis because of within-group morphologic heterogeneity. While induced velocities for this group paralleled the observed downward trend across all developmental stages, mean velocity for the 4-16-cell stage did not differ significantly ($p=0.59$) between the 2 groups. Additionally, the variance among matched cohorts cultured in KSOM+AA and M16 and assayed at the 1-cell and 2-cell stages was not significantly different ($p=0.67$ and $p=0.87$, respectively). However, among embryos assayed at the 4-16-cell/morula and early-blastocyst stages, those cultured in KSOM+AA had significantly lower variance than matched cohorts cultured in M16 ($p<0.0012$ and $p<0.015$, respectively).

Immediately after OET assay, embryos appeared slightly contracted and granular. This effect on embryo morphology appears to be attributable to the EP medium, rather than OET assay itself. To better understand whether potential adverse effects on the embryos due to EP and OET were reversible, embryos that underwent initial OET assay (T=0) at the 1-cell, 2-cell, 8-cell and early blastocyst stages, were recovered from the OET device, returned to incubation in KSOM+AA medium, and photographed every 24 hours thereafter. Ninety to 95% of embryos in each cohort continued to develop normally to the hatched blastocyst stage. Long term exposure to EP media (5-24 hrs.) did result in eventual embryo death and the speeds of all embryos assayed after this long term culture were <5 μm/s.

It can be seen that OET-DEP provides a powerful DEP manipulation and interrogation platform, as compared to conventional methods, that provides the ability to move the embryos in real time and allows one to measure the magnitude of attraction (or repulsion) that the individual embryo exhibits in response to the DEP force provided by the OET platform. The ability to not only measure the DEP response of the embryos allows one to perform additional functions such as embryo sorting (a specific embryo exhibiting a specific response can be selected and removed from a surrounding cohort) and improved optical interrogation (the embryo can be manipulated to allow for different perspectives which may aid in determining characteristics such as the number of cells within the embryo or the location of specific intra-embryo structures). Furthermore, OET can be used to guide embryo selection for IVF because the process can distinguish between morphologically similar appearing embryos at any given stage since the embryo with the most negative response to OET is likeliest to be the most developmentally mature and/or viable embryo that should be selected for transfer. This approach is supported by both cross-developmental-stage, and, developmental-stage-matched, cross-medium comparisons (KSOM+AA and M16 cultured embryos).

Example 2

A second illustration of the functionality of OET-DEP devices and methods is shown with the separation of viable motile and non-motile sperm from non-viable sperm. The use of intracytoplasmic sperm injection (ICSI) in combination with in vitro fertilization is increasingly used in cases of male-factor infertility. In this procedure, fertilization is achieved by injecting a single sperm directly into the oocyte (egg). Since the introduction of ICSI in 1992, this procedure has rapidly gained acceptance, and now accounts for approximately 3% of U.S. births. A major concern related to ICSI is sperm selection, because the quality of the individual sperm that ultimately fertilizes the oocyte is essential to the success of the procedure. Selection of non-viable sperm, for example, will not result in fertilization or will produce an embryo that will ultimately be non-viable and a valuable oocyte is wasted.

The selection of viable sperm for ICSI is challenging, and generally sperm motility is the selection criteria as an indicator of viability. Sperm morphology has been shown to be a poor index for sperm viability. Furthermore, motility does not exclude the presence of significant DNA damage. In addition, for patients who have limited, or even non-motile sperm (asthenospermia), selection of viable sperm on the basis of sperm motility can be virtually impossible. In addition, reduced sperm motility is also often encountered in sperm samples that have been cryopreserved (frozen) before use. Upon thawing of the sample, previously-motile sperm can be rendered non-motile. While for many patients a sizable fraction of the sample may still be viable but distinguishing between viable from non-viable sperm can be challenging absent motility.

Current sperm viability assays are limited by subjectivity, sensitivity, and potential toxicity. The Trypan Blue dye exclusion test is a gold-standard cell viability assay, but its toxicity precludes subsequently using sperm exposed to Trypan Blue for ICSI. Another dye-based assay, eosin-nigrosin staining, involves an air-drying step which also renders the tested sperm unavailable for further use. Ultimately, the current standard approach to sperm selection for use in ICSI procedures is based on the presence of motility, and, in the absence of this, sperm morphology. However, sperm motility and morphology may be inadequate to identify viable and healthy sperm.

In order to demonstrate the apparatus and methods for the separation of sperm, experiments were conducted to verify the feasibility of using DEP forces to distinguish between viable and non-viable sperm, even if the sperm are non-motile.

Sperm sorting was performed inside a microfluidic chamber embedded within a glass chip slide. Its lower surface is formed by a 2.5 cm×1.5 cm×1 mm glass slide coated with a 100-nm-thick film of indium-tin-oxide and a 1-μm-thick film of amorphous silicon. The upper surface of the microfluidic chamber was also formed by a glass slide with an indium-tin-oxide film. The two surfaces of the OET microfluidic chamber were separated by a 100-μm-thick spacer, creating a chamber filled with the fluid suspension of cells to be sorted. The OET sperm sorting chip was placed under an upright microscope to interface with the other components of the OET apparatus. Live sperm manipulation was viewed using a closed-circuit digital camera.

OET actuation patterns to produce dielectrophoretic forces was provided by a 10-mW, 635-nm diode laser that was focused onto the lower surface of the OET Chip using a 10× objective lens. The output of the laser was attenuated resulting in an intensity of 40 mW/cm$^2$ incident upon the OET device. Since the laser was directed through the glass substrate underneath the a-Si layer, the sperm samples were further screened from the actuation laser by the absorption of the light in the a-Si layer. Sperm moved in response to the location of the optical pattern across the OET device surface. The electric field was produced by biasing the device at 3.2 $V_{rms}$ at 100 kHz.

Semen specimens were obtained from six donors and evaluated using OET. The adequacy of each specimen was confirmed by the presence of motile sperm in the sample, indicating live sperm. In order to determine the viability of non-motile cells, the samples were mixed in a 1:1 volume ratio with 0.4% Trypan Blue dye in DI water, and incubated at room temperature for 3 minutes. The sperm/Trypan mixture was then diluted approximately 100 times by adding isotonic solution. The conductivity of the diluted sperm solution was adjusted to be 6.5 mS/m for all samples. A 20-μL aliquot of the Trypan-stained sperm sample was pipetted into the PEG-coated OET devices. Over a 15-minute period, 55 distinct sperm were evaluated from each donor. As a positive control, five motile sperm were trapped using OET, verifying that a positive OET response was induced on these viable sperm. The OET-induced velocity of 25 non-motile sperm that excluded the Trypan Blue dye was also evaluated. These sperm are live, but non-motile. In addition, the OET-induced velocity of 25 dead sperm was measured. Here, dead sperm refer to the cells that experienced negative OET or no OET response. Most of these sperm were stained by Trypan Blue (Trypan Blue positive), although a few were not stained (Trypan Blue negative). All velocity measurements were done using an applied bias of 9 Vpp at 100 kHz.

A total of 330 individual sperm from the 6 separate subjects were assayed. All (100%) of the motile sperm visualized in each specimen were Trypan Blue negative, and all of those assayed (N=25) experienced positive OET. All (100%) sperm experiencing positive OET were Trypan Blue negative (N=150). The Trypan-Blue-positive sperm demonstrated either no response (54%) or a weak repulsive response (46%)

to the OET manipulation pattern. A few Trypan-Blue-negative sperm (15%) demonstrated no response to OET actuation, suggesting that these sperm are also dead.

The velocity measurements on the live non-motile sperm and dead sperm were observed. The average velocity of live non-motile sperm in the OET device is 8.0±3.9 μm/s, averaged over 150 cells from 6 separate donors. The average velocity of dead sperm is −1.0±1.2 μm/s with the negative value indicating a negative OET force. The dead Trypan-Blue-positive sperm exhibited some variability in their OET response, exhibiting either weak negative OET (54%) or no response to the OET pattern (46%). However, no Trypan-Blue-positive sperm exhibited a positive OET response. Thus, these results show a clear separation of the cell subpopulations.

The results indicated that the OET DEP-based sperm sorting platform can distinguish individual viable sperm from non-viable motile and non-motile sperm within a heterogeneous sample. Present results using OET-DEP to identify viable sperm compare favorably with gold-standard dye exclusion sperm viability tests. There was remarkable concordance between the two tests, and internal consistency. Not a single sperm, designated 'non-viable' by the vital dye exclusion test (Trypan positive), was designated 'viable' (i.e. false positive) by the OET platform. This was also accomplished without addition of chemical agents and without direct physical contact with the sperm.

Accordingly, the sperm sorting method and platform, using OET-DEP, is comparable, if not superior, to the gold standard vital dye exclusion assays. Furthermore, the proposed platform, uniquely, allows individual cell manipulation and isolation within a sterile microchip, for integrated use with ICSI.

By way of example, and not of limitation, among other things, the following has been shown and observed:

For example, among embryos, it has been shown that a more negative DEP response is associated with a more developmentally mature morphologic state of development. Current embryo selection practice is based on selecting the embryo with the most developmentally mature morphology, based on the assumption that, because all in vitro fertilized embryos are "created" at the same time, the embryo that is able to develop the most, in a standard period of time, is presumed to be the healthiest. More particularly it has been shown:

1. As embryos mature (developmentally and morphologically), their DEP response trends from positive (early development) to negative (advanced development).

2. Among any cohort of otherwise indistinguishable (based on current gold standard embryo assessment criteria), some embryos within the cohort respond more negatively than others, and that the most negatively responding embryos are those that are the most developmentally mature.

3. As an embryo dies, its DEP response slowly drifts to zero (just as occurs with all dead single-cell organisms). While all dead embryos respond "neutrally" to DEP, the DEP response is actually moot, as embryo morphology clearly indicates that the embryo is dying/dead. As with single cell organisms, a "dead" target will eventually respond neutrally.

4. Among obviously live embryos, a neutral response represents a natural inflection point along the continuum from positive to negative. Any one of these embryos responding with a "neutral" response will be obviously "alive", and simply cannot be confused for a "dead" embryo, since the morphology of live and dead embryos is so obviously different. Again, for obviously "live" embryos (where "live" status is based on conventional morphologic criteria), a neutral response is an "inflection point", and does not mean "dead", as it does for embryos that look obviously "dead". To summarize, when live embryos respond "neutrally" to DEP, that is, when they are neither attracted to, nor repulsed by DEP, they actually still do respond in a unique fashion: many (but not all) surprisingly "spin" in place. Because they stay in place, and cannot be moved in an X-Y direction, their net DEP response is "zero". But, based on their obvious normal morphology and the fact that many spin in place.

5. It is possible to identify and retrieve the single most developmentally mature embryo among any cohort of otherwise indistinguishable embryos, simply by performing a DEP assay on each embryo, and selecting the one that responds most negatively.

6. For sperm selection, the same approach as for embryo selection can be used. However, with sperm, the most "most viable" (and/or presumably "most developmentally mature") is the sperm that responds with the most positive (attractive) response to the DEP field. Practically speaking, the DEP assay response of many sperm is assessed, and, the one(s) with the most positive response are isolated for consideration of use with ICSI (Intracytoplasmic sperm injection).

7. With embryos, it is possible to "screen" the candidate embryos, to exclude any that appear abnormal, or developmentally immature. Mainly because in the clinical setting, the number of candidate embryos is usually <15.

8. When using DEP to assess sperm, it is desirable to exclude obviously "bad" sperm from consideration. However, since sperm assay (if automated, using our chips) will involve hundreds to tens of thousands, it may likely not be possible to individually "pre-screen" target sperm. This is not a problem, as long as, before making a "final selection" of sperm based on their DEP response, the user is reminded to visually assess all of the sperm identified by DEP assay (based on a high-positive response) as the "best" in the group, to exclude morphologically-aberrant sperm, and/or, sperm that vary significantly in size (as large differences in size can account for large differences in DEP assay response; although, in practice, most sperm in a single sample are very similar in size).

9. In order for DEP assay results to be interpretable among different practitioners, it is desirable to standardize all features of the DEP assay described above, and also the specific technique used to measure DEP response. For example, measured DEP response preferably should be based on more than one measurement for each target, while imposing other criteria, such as, for example, that measurements should be repeated until at least 2 (or 3) measured DEP responses do not differ by more than 5%; again, preferably always under "standardized conditions" of the medium and environment. In other words, it is preferable that all DEP assays, including the viability assays described herein, always be performed under "standardized" conditions. The most accurate interpretation of all DEP assay responses will result when the assay conditions are known, and can be compared to a reference response under a particular combination of conditions.

10. "Chromosomal aneuploidy" of sperm (or embryos), would be useful to detect before the sperm is used for ICSI (or before, for example, the embryo is transferred to a woman's uterus). Chromosomal aneuploidy (abnormality in the number of whole chromosomes) results typically from nondisjunction events germ cell meiosis. The result of this is sperm that are either disomic or nullisomic for a particular chromosome. From a reproductive standpoint, this is important in that fertilization with these sperm results in embryos which are either monosomic or trisomic; many of these embryos are spontaneously aborted during pregnancy (resulting in couples presenting with recurrent pregnancy loss) or in offspring which are syndromic (Turner, Down, or Klinefelter Syndromes for example). As such, evaluation of sperm for abnormal numbers of aneuploid cells in couples with normal somatic karyotype presenting with (a) recurrent pregnancy loss (b) prior birth of an infant with a chromosomal disorder of numerical abnormality seems warranted.

11. It is believed that the relative DEP response can be used to detect chromosomal aneuploidy. We expect that extra (or fewer) chromosomes would confer a different net dielectric potential to the biological target. A net gain, or loss, of chromosomes, relative to a normal complement, will likely result in aberrant physiologic unction of the cell/embryo, which will affect its dielectric potential. Also, as with the disease Cystic Fibrosis, aberrant chromosomes result in aberrant physiology, membrane ion channels, and membrane electrical currents, all of which result in aberrant net target dielectric potential. In other words, anything that impacts a target's dielectric potential will undoubtedly affect the target's DEP response.

12. It is envisioned that assaying DEP response will be useful to detect and identify grossly aberrant target cells within a large sample, provided that we have "standards" against which to compare any sample. With sperm, for example, sperm from men of different age ranges would be assayed to determine what should be considered a "normal" response. Also, sperm from men of different ages that vary in other key ways should be assessed to improve the sensitivity and specificity of the DEP assay. For example, sperm from healthy/fertile men of a certain age range would represent one standard, and sperm from men of a certain age range with known or suspected infertility would make up another "standard" to which a patient's sample would be compared.

DEP response of sperm (or embryos, etc) could even vary by age, health status, chromosome status (e.g. Aneuploidy), or sex (embryos, or other cells). We also believe that DEP assay could predict embryo (or sperm) gender based on DEP response. For sperm, this could be explained by the fact that Y chromosome sperm (which will always make a male), have slightly less DNA content than X chromosome sperm (will always make a female.). (Y chromosomes are smaller than X chromosomes). Since DNA is also a source of electric charge, it is certainly possible that DEP could discern a difference between X and Y sperm, or male and female embryos. Also, it is certainly possible that male and female embryos exhibit different electric profiles at certain points in their development, and such differences could be discerned by DEP response.

13. DEP response should very likely be able to detect different states of malignancy ("cancer") in target cells, ranging from malignant to pre-malignant changes. Malignant changes are invariably associated with aberrant states of physiologic activity within the cell (usually "hyper-activity"). Increased physiologic activity could be expected to result in a different dielectric state for the particular cell, which, could be discerned by DEP assay. To the extent that a particular population of target cells are normally homogenous, an automated assay using one of the devices described herein, could screen a large number of cells to determine what fraction, if any, respond "aberrantly" to the OET assay. Again, it is important to have validated "standards" against which to compare an individual sample.

14. Our method of sorting and selecting embryos is expected to yield in-vitro fertilization success rates preferably in the range from 25% to 60%, more preferably from 25% to 30%, more preferably from 30% to 35%, more preferably from 35% to 40%, more preferably from 40% to 45%, more preferably from 45% to 50%, more preferably from 50% to 55%, and more preferably from 55% to 60%.

Accordingly, various embodiments of the present invention include, but are not limited to:

1. An apparatus for sorting cells or particles by light induced dielectrophoresis (DEP), the apparatus comprising: (a) a fluidic chamber having a first surface and a second surface configured for retaining in the fluidic chamber a liquid containing a population of particles or cells to be sorted; (b) a photoconductive area on said first or said second surface configured for conversion of received light to a local electric field in the vicinity of the received light; (c) an inlet configured for receiving a sample liquid containing a population of particles or cells to be sorted; and (d) a plurality of outlet channels spaced-apart at relative distances in relation to the position of the photoconductive area of the fluidic chamber.

2. An apparatus according to embodiment 1: wherein particles or cells in the fluidic chamber are responsive to the electric field as a function of viability; wherein the particles or cells are retrievable through specific outlet channels in the plurality of outlet channels as a function of response to the electric field; and wherein a specific outlet channel through which a said particle or cell is retrievable is indicative of relative viability of the particle or cell.

3. An apparatus according to embodiment 2: wherein said population of particles or cells comprises a population of embryos; and wherein a more negative response to the electric field indicates a more viable embryo in the population of embryos.

4. An apparatus according to embodiment 3, wherein a negative response to the electric field comprises repulsion to the electric field.

5. An apparatus according to embodiment 2 or 3, wherein viability comprises a characteristic selected from the group consisting of developmental maturity, health, and physiologic state.

6. An apparatus according to embodiment 1, further comprising: a light source to provide the light to the photoconductive area; and a light pattern controller configured for controlling output and pattern of light provided to the photoconductive area from the light source.

7. An apparatus according to embodiment 7, further comprising an imaging device for observing particle or cell sorting.

8. An apparatus for sorting cells or particles by light induced dielectrophoresis (DEP), the apparatus comprising: (a) a fluidic chamber having a first surface and a second surface configured for retaining in the fluidic chamber a liquid containing a population of particles or cells to be sorted; (b) a photoconductive area on said first or said second surface configured for conversion of received light to a local electric field in the vicinity of the received light; and (c) an extraction port configured for manual extraction of a particle or cell from the fluidic chamber using a micropipette; (d) wherein said extraction port comprises: (i) a beveled circular edge in the first surface; and (ii) a beveled circular edge in the second surface, the beveled circular edge in the second surface opposing the beveled circular edge in the first surface.

9. An apparatus according to embodiment 8, wherein particles or cells in the fluidic chamber are responsive to the electric field as a function of viability.

10. An apparatus according to embodiment 9: wherein the population of particles or cells comprises a population of embryos; and wherein a more negative response to the electric field indicates a more viable embryo in the population of embryos.

11. An apparatus according to embodiment 10, wherein a negative response to the electric field comprises repulsion to the electric field.

12. An apparatus according to embodiment 9 or 10, wherein viability comprises a characteristic selected from the group consisting of developmental maturity, health, and physiologic state.

13. An apparatus according to embodiment 8, further comprising: a light source to provide the light to the photoconductive area; and a light pattern controller configured for controlling output and pattern of light provided to the photoconductive area from the light source.

14. An apparatus according to embodiment 13, further comprising an imaging device for observing particle or cell sorting.

15. An apparatus for sorting embryos by light induced dielectrophoresis (DEP), the apparatus comprising: (a) a fluidic chamber having a first surface and a second surface configured for retaining in the fluidic chamber a liquid containing a population of embryos; (b) a photoconductive area on said first or said second surface configured for conversion of received light to a local electric field in the vicinity of the received light; and (c) an extraction port configured for manual extraction of an embryo from the fluidic chamber using a micropipette; and (d) wherein said extraction port comprises: (i) a beveled circular edge in the first surface; and (ii) a beveled circular edge in the second surface, the beveled circular edge in the second surface opposing the beveled circular edge in the first surface.

16. An apparatus according to embodiment 15: wherein embryos in the fluidic chamber are responsive to the electric field as a function of viability; and wherein a more negative response to the electric field indicates a more viable embryo in the population of embryos.

17. An apparatus according to embodiment 16, wherein viability comprises a characteristic selected from the group consisting of developmental maturity, health, and physiologic state.

18. An apparatus according to embodiment 15, wherein a negative response to the electric field comprises repulsion to the electric field.

19. An apparatus according to embodiment 15, further comprising: a light source to provide the light to the photoconductive area; and a light pattern controller configured for controlling output and pattern of light provided to the photoconductive area from the light source.

20. An apparatus according to embodiment 19, further comprising an imaging device for observing embryo sorting.

21. An apparatus for sorting embryos by light induced dielectrophoresis (DEP), the apparatus comprising: (a) a fluidic chamber having a first surface and a second surface configured for retaining in the fluidic chamber a liquid containing a population of embryos; (b) a photoconductive area on said first or said second surface configured for conversion of received light to a local electric field in the vicinity of the received light; and (c) an extraction port configured for manual extraction of an embryo from the fluidic chamber using a micropipette; and (d) wherein said extraction port comprises: (i) a beveled circular edge in the first surface; and (ii) a beveled circular edge in the second surface, the beveled circular edge in the second surface opposing the beveled circular edge in the first surface; (e) wherein embryos in the fluidic chamber are responsive to the electric field as a function of viability; and (f) wherein a more negative response to the electric field indicates a more viable embryo in the population of embryos.

22. An apparatus according to embodiment 21, wherein viability comprises a characteristic selected from the group consisting of developmental maturity, health, and physiologic state.

23. An apparatus according to embodiment 21, wherein a negative response to the electric field comprises repulsion to the electric field.

24. An apparatus according to embodiment 21, further comprising: a light source to provide the light to the photoconductive area; and a light pattern controller configured for controlling output and pattern of light provided to the photoconductive area from the light source.

25. An apparatus according to embodiment 24, further comprising an imaging device for observing embryo sorting.

26. A method for sorting cells or particles by light induced dielectrophoresis (DEP), the method comprising: (a) providing a fluidic chamber, the fluidic chamber comprising: (i) a first surface and a second surface configured for retaining in the fluidic chamber a liquid containing a population of particles or cells to be sorted; (ii) a photoconductive area on said first or said second surface configured for conversion of received light to a local electric field in the vicinity of the received light; (iii) an inlet configured for receiving a sample containing a population of particles or cells to be sorted; and (iv) a plurality of outlet channels spaced-apart at relative distances in relation to the position of the photoconductive area of the fluidic chamber; (b) introducing into the fluidic chamber a sample liquid containing a population of particles or cells to be sorted; (c) exposing at least a portion of the photoconductive area to a source of light and inducing the local electric field; and (d) sorting the particles or cells through said outlet channels as a function of response to the electric field.

27. A method according to embodiment 26: wherein the particles or cells are responsive to the electric field as a function of viability; and wherein a specific outlet channel through which a said particle or cell is retrievable is indicative of relative viability of the particle or cell.

28. A method according to embodiment 27: wherein said population of particles or cells comprises a population of embryos; and wherein a more negative response to the electric field indicates a more viable embryo in the population of embryos.

29. A method according to embodiment 28, wherein a negative response to the electric field comprises repulsion to the electric field.

30. A method according to embodiment 27 or 28, wherein viability comprises a characteristic selected from the group consisting of developmental maturity, health, and physiologic state.

31. A method for sorting cells or particles by light induced dielectrophoresis (DEP), the method comprising: (a) providing a fluidic chamber, the fluidic chamber comprising: (i) a first surface and a second surface configured for retaining in the fluidic chamber a liquid containing a population of particles or cells to be sorted; (ii) a photoconductive area on said first or said second surface configured for conversion of received light to a local electric field in the vicinity of the received light; (iii) an extraction port configured for manual extraction of a particle or cell from the fluidic chamber using a micropipette; (iv)

the extraction port comprising a beveled circular edge in the first surface, and a beveled circular edge in the second surface, the beveled circular edge in the second surface opposing the beveled circular edge in the first surface; (e) introducing into the fluidic chamber a sample liquid containing a population of particles or cells to be sorted; (f) exposing at least a portion of the photoconductive area to a source of light and inducing the local electric field; and (g) selecting a particle or cell for extraction as a function of response to the electric field; and (h) extracting the selected particle or cell through the extraction port.

32. A method according to embodiment 31, wherein the particles or cells are responsive to the electric field as a function of viability.

33. A method according to embodiment 31: wherein said population of particles or cells comprises a population of embryos; and wherein a more negative response to the electric field indicates a more viable embryo in the population of embryos.

34. A method according to embodiment 33, wherein a negative response to the electric field comprises repulsion to the electric field.

35. A method according to embodiment 32 or 33, wherein viability comprises a characteristic selected from the group consisting of developmental maturity, health, and physiologic state.

36. A method for sorting embryos by light induced dielectrophoresis (DEP), the method comprising: (a) providing a fluidic chamber, the fluidic chamber comprising: (i) a first surface and a second surface configured for retaining in the fluidic chamber a liquid containing a population of embryos; (ii) a photoconductive area on said first or said second surface configured for conversion of received light to a local electric field in the vicinity of the received light; (iii) an extraction port configured for manual extraction of an embryo from the fluidic chamber using a micropipette; (iv) the extraction port comprising a beveled circular edge in the first surface, and a beveled circular edge in the second surface, the beveled circular edge in the second surface opposing the beveled circular edge in the first surface; (e) introducing into the fluidic chamber a sample liquid containing population of embryos; (f) exposing at least a portion of the photoconductive area to a source of light and inducing the local electric field; and (g) selecting an embryo for extraction as a function of response to the electric field; and (h) extracting the selected embryo through the extraction port.

37. A method according to embodiment 36: wherein embryos in the fluidic chamber are responsive to the electric field as a function of viability; and wherein a more negative response to the electric field indicates a more viable embryo in the population of embryos.

38. A method according to embodiment 37, wherein viability comprises a characteristic selected from the group consisting of developmental maturity, health, and physiologic state.

39. An apparatus according to embodiment 37, wherein a negative response to the electric field comprises repulsion to the electric field.

40. A method for sorting embryos by light induced dielectrophoresis (DEP), the method comprising: (a) providing a fluidic chamber, the fluidic chamber comprising: (i) a first surface and a second surface configured for retaining in the fluidic chamber a liquid containing a population of embryos; (ii) a photoconductive area on said first or said second surface configured for conversion of received light to a local electric field in the vicinity of the received light; (iii) an extraction port configured for manual extraction of an embryo from the fluidic chamber using a micropipette; (iv) the extraction port comprising a beveled circular edge in the first surface, and a beveled circular edge in the second surface, the beveled circular edge in the second surface opposing the beveled circular edge in the first surface; (e) introducing into the fluidic chamber a sample liquid containing population of embryos; (f) exposing at least a portion of the photoconductive area to a source of light and inducing the local electric field; (g) selecting an embryo for extraction as a function of response to the electric field; (h) wherein embryos in the fluidic chamber are responsive to the electric field as a function of viability; and (i) wherein a more negative response to the electric field indicates a more viable embryo in the population of embryos; and (j) extracting the selected embryo through the extraction port.

41. A method according to embodiment 40, wherein viability comprises a characteristic selected from the group consisting of developmental maturity, health, and physiologic state.

42. An apparatus according to embodiment 40, wherein a negative response to the electric field comprises repulsion to the electric field.

43. A method for sorting cells or particles by light induced dielectrophoresis (DEP), the method comprising: (a) identifying traits of interest of a population of particles or cells in a sample; (b) exposing the sample to DEP; (c) measuring the response of the particles or cells to the DEP; (d) indexing the response measurements; (e) correlating the indexed response measurements with specific traits; (f) separating particles or cells with desired traits from a population of particles or cells based on the correlated response to DEP; and (g) isolating and extracting the separated particles or cells.

44. A method according to embodiment 43: wherein said population of particles or cells comprises a population of embryos; wherein a said trait of interest is viability; and wherein a more negative response to the DEP indicates a more viable embryo in the population of embryos.

45. A method according to embodiment 44, wherein a negative response to the DEP comprises repulsion to the DEP.

46. A method according to embodiment 44, wherein viability comprises a characteristic selected from the group consisting of developmental maturity, health, and physiologic state.

47. A method for sorting cells or particles by light induced dielectrophoresis (DEP), the method comprising: (a) identifying targeted characteristics of a population of particles or cells in a sample; (b) exposing the sample to a range of DEP field intensities; (c) measuring the response of the particles or cells to the range of DEP field intensities; (d) correlating the targeted characteristics with the DEP response measurements; and (e) extracting particles or cells with the targeted characteristics from the sample.

48. A method according to embodiment 47: wherein said population of particles or cells comprises a population of embryos; wherein a said targeted characteristic is viability; and wherein a more negative response to the DEP indicates a more viable embryo in the population of embryos.

49. A method according to embodiment 48, wherein a negative response to the DEP comprises repulsion to the DEP.

50. A method according to embodiment 48, wherein viability comprises a characteristic selected from the group consisting of developmental maturity, health, and physiologic state.

51. A method for sorting cells or particles by light induced dielectrophoresis (DEP), the method comprising: (a) identifying targeted characteristics of a population of particles or cells in a sample; (b) exposing the sample to a range of DEP field intensities; (c) measuring the response of the particles or cells to the range of DEP field intensities; (d) correlating optimum DEP responses of targets with optimum DEP field characteristics; (e) separating targets with traits of interest from a population of targets with optimum DEP field characteristics; and (f) extracting separated targets according to strength of target response to optimized DEP fields.

52. A method according to embodiment 51: wherein said population of particles or cells comprises a population of embryos; wherein a said targeted characteristic is viability; and wherein a more negative response to the DEP indicates a more viable embryo in the population of embryos.

53. A method according to embodiment 52, wherein a negative response to the DEP comprises repulsion to the DEP.

54. A method according to embodiment 52, wherein viability comprises a characteristic selected from the group consisting of developmental maturity, health, and physiologic state.

55. A method comprising sorting embryos in a population of embryos and selecting, from the sorted population, an embryo for in-vitro fertilization (IVF) where the IVF has a success rate from 25% to 60%.

56. A method according to embodiment 55, wherein the success rate is from 25% to 30%.

57. A method according to embodiment 55, wherein the success rate is from 30% to 35%.

58. A method according to embodiment 55, wherein the success rate is from 35% to 40%.

59. A method according to embodiment 55, wherein the success rate is from 40% to 45%.

60. A method according to embodiment 55, wherein the success rate is from 45% to 50%.

61. A method according to embodiment 55, wherein the success rate is from 50% to 55%.

62. A method according to embodiment 55, wherein the success rate is from 55% to 60%.

Although the description herein contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art. In the appended claims, reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present disclosure. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. An apparatus for sorting cells or particles by light induced dielectrophoresis (DEP), the apparatus comprising:
   (a) a fluidic chamber having a first surface and a second surface configured for retaining in the fluidic chamber a liquid containing a population of particles or cells to be sorted;
   (b) a photoconductive area on said first or said second surface configured for conversion of received light to a local electric field in the vicinity of the received light;
   (c) an inlet configured for receiving a sample liquid containing a population of particles or cells to be sorted; and
   (d) a plurality of outlet channels spaced-apart at relative distances in relation to the position of the photoconductive area of the fluidic chamber;
   (e) wherein the particles or cells are retrievable through specific outlet channels in the plurality of outlet channels as a function of response to the electric field;
   (f) wherein a specific outlet channel through which a said particle or cell is retrievable is indicative of relative magnitude of the response of the particle or cell to the electric field; and
   (g) an extraction port configured for manual extraction of a particle or cell from the fluidic chamber using a micropipette.

2. An apparatus as recited in claim 1, wherein said extraction port comprises:
   a beveled circular edge in the first surface; and
   a beveled circular edge in the second surface, the beveled circular edge in the second surface opposing the beveled circular edge in the first surface.

3. An apparatus for sorting embryos by light induced dielectrophoresis (DEP), the apparatus comprising:
   (a) a fluidic chamber having a first surface and a second surface configured for retaining in the fluidic chamber a liquid containing a population of embryos; and
   (b) a photoconductive area on said first or said second surface configured for conversion of received light to a local electric field in the vicinity of the received light;
   (c) wherein embryos in the fluidic chamber are responsive to the electric field as a function of viability;
   (d) wherein a more negative response to the electric field indicates a more viable embryo in the population of embryos; and
   (e) an extraction port configured for manual extraction of a particle or cell from the fluidic chamber using a micropipette.

4. An apparatus as recited in claim 3, wherein said extraction port comprises:
   a beveled circular edge in the first surface; and
   a beveled circular edge in the second surface, the beveled circular edge in the second surface opposing the beveled circular edge in the first surface.

5. An apparatus as recited in claim 3, wherein viability comprises a characteristic selected from the group consisting of developmental maturity, health, and physiologic state.

6. An apparatus as recited in claim 3, wherein a negative response to the electric field comprises repulsion to the electric field.

7. An apparatus as recited in claim 3, further comprising:
   a light source to provide the light to the photoconductive area; and
   a light pattern controller configured for controlling output and pattern of light provided to the photoconductive area from the light source.

8. An apparatus as recited in claim 7, further comprising an imaging device for observing embryo sorting.

9. A method for sorting cells or particles by light induced dielectrophoresis (DEP), the method comprising:
   (a) providing a fluidic chamber, the fluidic chamber comprising:
      (i) a first surface and a second surface configured for retaining in the fluidic chamber a liquid containing a population of particles or cells to be sorted;
      (ii) a photoconductive area on said first or said second surface configured for conversion of received light to a local electric field in the vicinity of the received light;

(iii) an extraction port configured for manual extraction of a particle or cell from the fluidic chamber using a micropipette;

(iv) the extraction port comprising a beveled circular edge in the first surface, and a beveled circular edge in the second surface, the beveled circular edge in the second surface opposing the beveled circular edge in the first surface;

(b) introducing into the fluidic chamber a sample liquid containing a population of particles or cells to be sorted;

(c) exposing at least a portion of the photoconductive area to a source of light and inducing the local electric field; and (d) selecting a particle or cell for extraction as a function of response to the electric field; and (e) extracting the selected particle or cell through the extraction port.

10. A method as recited in claim 9, wherein the particles or cells are responsive to the electric field as a function of viability.

11. A method as recited in claim 9:
wherein said population of particles or cells comprises a population of embryos; and
wherein a more negative response to the electric field indicates a more viable embryo in the population of embryos.

12. A method as recited in claim 11, wherein a negative response to the electric field comprises repulsion to the electric field.

13. A method as recited in claim 10 or 11, wherein viability comprises a characteristic selected from the group consisting of developmental maturity, health, and physiologic state.

14. A method for sorting embryos by light induced dielectrophoresis (DEP), the method comprising:
(a) providing a fluidic chamber, the fluidic chamber comprising:
(i) a first surface and a second surface configured for retaining in the fluidic chamber a liquid containing a population of embryos;
(ii) a photoconductive area on said first or said second surface configured for conversion of received light to a local electric field in the vicinity of the received light;
(iii) an extraction port configured for manual extraction of an embryo from the fluidic chamber using a micropipette;
(iv) the extraction port comprising a beveled circular edge in the first surface, and a beveled circular edge in the second surface, the beveled circular edge in the second surface opposing the beveled circular edge in the first surface;
(b) introducing into the fluidic chamber a sample liquid containing population of embryos;
(c) exposing at least a portion of the photoconductive area to a source of light and inducing the local electric field; and
(d) selecting an embryo for extraction as a function of response to the electric field; and
(e) extracting the selected embryo through the extraction port.

15. A method as recited in claim 14:
wherein embryos in the fluidic chamber are responsive to the electric field as a function of viability; and
wherein a more negative response to the electric field indicates a more viable embryo in the population of embryos.

16. A method as recited in claim 15, wherein viability comprises a characteristic selected from the group consisting of developmental maturity, health, and physiologic state.

17. A method as recited in claim 15, wherein a negative response to the electric field comprises repulsion to the electric field.

18. A method for sorting embryos by light induced dielectrophoresis (DEP), the method comprising:
(a) providing a fluidic chamber, the fluidic chamber comprising:
(i) a first surface and a second surface configured for retaining in the fluidic chamber a liquid containing a population of embryos;
(ii) a photoconductive area on said first or said second surface configured for conversion of received light to a local electric field in the vicinity of the received light;
(iii) an extraction port configured for manual extraction of an embryo from the fluidic chamber using a micropipette;
(iv) the extraction port comprising a beveled circular edge in the first surface, and a beveled circular edge in the second surface, the beveled circular edge in the second surface opposing the beveled circular edge in the first surface;
(b) introducing into the fluidic chamber a sample liquid containing population of embryos;
(c) exposing at least a portion of the photoconductive area to a source of light and inducing the local electric field;
(d) selecting an embryo for extraction as a function of response to the electric field;
(e) wherein embryos in the fluidic chamber are responsive to the electric field as a function of viability; and
(f) wherein a more negative response to the electric field indicates a more viable embryo in the population of embryos; and
(g) extracting the selected embryo through the extraction port.

19. A method as recited in claim 18, wherein viability comprises a characteristic selected from the group consisting of developmental maturity, health, and physiologic state.

20. A method as recited in claim 18, wherein a negative response to the electric field comprises repulsion to the electric field.

21. A method for sorting cells or particles by light induced dielectrophoresis (DEP), the method comprising:
(a) identifying traits of interest of a population of particles or cells in a sample;
(b) exposing the sample to DEP;
(c) measuring the response of the particles or cells to the DEP;
(d) indexing the response measurements;
(e) correlating the indexed response measurements with specific traits;
(f) separating particles or cells with desired traits from a population of particles or cells based on the correlated response to DEP; and
(g) isolating and extracting the separated particles or cells.

22. A method as recited in claim 21:
wherein said population of particles or cells comprises a population of embryos;
wherein a said trait of interest is viability; and
wherein a more negative response to the DEP indicates a more viable embryo in the population of embryos.

23. A method as recited in claim 22, wherein a negative response to the DEP comprises repulsion to the DEP.

24. A method as recited in claim 22, wherein viability comprises a characteristic selected from the group consisting of developmental maturity, health, and physiologic state.

25. A method for sorting cells or particles by light induced dielectrophoresis (DEP), the method comprising:
(a) identifying targeted characteristics of a population of particles or cells in a sample;
(b) exposing the sample to a range of DEP field intensities;
(c) measuring the response of the particles or cells to the range of DEP field intensities;
(d) correlating the targeted characteristics with the DEP response measurements; and
(e) extracting particles or cells with the targeted characteristics from the sample.

26. A method as recited in claim 25:
wherein said population of particles or cells comprises a population of embryos;
wherein a said targeted characteristic is viability; and
wherein a more negative response to the DEP indicates a more viable embryo in the population of embryos.

27. A method as recited in claim 26, wherein a negative response to the DEP comprises repulsion to the DEP.

28. A method as recited in claim 26, wherein viability comprises a characteristic selected from the group consisting of developmental maturity, health, and physiologic state.

29. A method for sorting cells or particles by light induced dielectrophoresis (DEP), the method comprising:
(a) identifying targeted characteristics of a population of particles or cells in a sample;
(b) exposing the sample to a range of DEP field intensities;
(c) measuring the response of the particles or cells to the range of DEP field intensities;
(d) correlating optimum DEP responses of targets with optimum DEP field characteristics;
(e) separating targets with traits of interest from a population of targets with optimum DEP field characteristics; and
(f) extracting separated targets according to strength of target response to optimized DEP fields.

30. A method as recited in claim 29:
wherein said population of particles or cells comprises a population of embryos;
wherein a said targeted characteristic is viability; and
wherein a more negative response to the DEP indicates a more viable embryo in the population of embryos.

31. A method as recited in claim 30, wherein a negative response to the DEP comprises repulsion to the DEP.

32. A method as recited in claim 30, wherein viability comprises a characteristic selected from the group consisting of developmental maturity, health, and physiologic state.

33. A process of sorting biological objects, said process comprising:
creating a laminar flow comprising a sample flow containing biological objects and an adjacent buffer flow; and
sorting non-motile, viable ones of said objects from non-viable ones of said objects in said sample flow by actively moving said non-motile, viable ones of said objects from said sample flow to said buffer flow.

34. The process of claim 33, wherein motile ones of said biological objects in said sample flow are able to swim from said sample flow to said buffer flow.

35. The process of claim 34, wherein said sorting comprises activating electrodes on a chamber in which the laminar flow is created, said electrodes creating dielectrophoretic (DEP) forces to which said non-motile, viable ones of said objects respond.

36. The process of claim 35, wherein said electrodes are fabricated electrodes.

37. The process of claim 35, wherein said electrodes are light activated virtual electrodes.

38. The process of claim 37, wherein said activating electrodes comprises:
applying a biasing voltage between a first electrode and a second electrode between which said laminar flow is created; and
directing a pattern of light onto a surface of a photoconductive layer on said first electrode, said virtual electrodes being activated at portions of said surface where said light is directed.

39. The process of claim 38, wherein said actively moving comprises trapping and then moving said non-motile, viable ones of said objects with said virtual electrodes.

40. The process of claim 38, wherein said actively moving comprises attracting said non-motile, viable ones of said objects to said virtual electrodes.

41. The process of claim 38, wherein said actively moving comprises scanning said pattern of light from said sample flow to said buffer flow.

42. The process of claim 41, wherein said actively moving further comprises turning off at least portions of said pattern of light to release said non-motile, viable objects in said buffer flow.

43. The process of claim 37 further comprising collecting said motile and said non-motile, viable ones of said objects in said sample flow.

44. The process of claim 37, wherein said objects are sperm.

45. A process of sorting embryos in a liquid disposed between a first electrode and a second electrode on which is disposed a photoconductive layer, said process comprising:
applying a biasing voltage between said first electrode and said second electrode;
activating virtual electrodes at a surface of said photoconductive layer by directing light onto said surface; and
sorting viable ones of said embryos in said liquid by maturity based on different responses of said embryos to dielectrophoretic (DEP) forces created by said virtual electrodes.

46. The process of claim 45, wherein a more negative response to said DEP forces corresponds to a more mature viable embryo.

47. The process of claim 45, further comprising selecting ones of said viable embryos having a negative response to said DEP forces.

48. The process of claim 45, further comprising selecting ones of said viable embryos having a most negative response to said DEP forces.

49. A process of sorting sperm or eggs in a liquid disposed between a first electrode and a second electrode on which is disposed a photoconductive layer, said process comprising:
applying a biasing voltage between said first electrode and said second electrode;
activating virtual electrodes at a surface of said photoconductive layer by directing light onto said surface; and
sorting viable ones of said sperm or eggs into categories based on a magnitude of responses of said sperm or eggs to dielectrophoretic (DEP) forces created by said virtual electrodes.

50. The process of claim 49, wherein:
said process is sorting sperm in said liquid, and
said sorting comprises sorting viable ones of said sperm into categories based on a magnitude of said responses of said viable ones of said sperm to said DEP forces.

51. The process of claim 49, wherein:
said process is sorting sperm in said liquid, and
a relative viability index of said viable ones of said sperm corresponds to a magnitude of an attractive or repulsive response of said viable ones of said sperm to said DEP forces.

52. The process of claim 51, wherein said relative viability index of said viable ones of said sperm corresponds to a magnitude of an attractive response of said viable ones of said sperm to said DEP forces.

53. The process of claim 49, wherein:
said process is sorting sperm in said liquid, and
said process further comprises selecting ones of said viable ones of said sperm exhibiting a greatest attractive or repulsive response to said DEP forces.

54. The process of claim 53, wherein said selecting ones of said viable ones of said sperm comprises selecting ones of said viable ones of said sperm exhibiting a greatest attractive response to said DEP forces.

55. The process of claim 49, wherein said sorting comprises sorting viable ones of said sperm or eggs into categories based on a magnitude of attractive or repulsive responses of said sperm or eggs to said DEP forces.

* * * * *